United States Patent
Sakamaki et al.

(10) Patent No.: US 11,866,527 B2
(45) Date of Patent: *Jan. 9, 2024

(54) PHOTOCURABLE COMPOSITION, CURED PRODUCT, AND DENTAL PRODUCT

(71) Applicant: MITSUI CHEMICALS, INC., Tokyo (JP)

(72) Inventors: Toshikazu Sakamaki, Tokyo (JP); Mai Kimura, Sodegaura (JP); Hiroki Murai, Ichihara (JP); Takaaki Hayashi, Funabashi (JP); Suguru Endo, Ichikawa (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/912,098

(22) PCT Filed: Mar. 22, 2021

(86) PCT No.: PCT/JP2021/011703
§ 371 (c)(1),
(2) Date: Sep. 16, 2022

(87) PCT Pub. No.: WO2021/193527
PCT Pub. Date: Sep. 30, 2021

(65) Prior Publication Data
US 2023/0137212 A1     May 4, 2023

(30) Foreign Application Priority Data

Mar. 27, 2020   (JP) ................... 2020-058696

(51) Int. Cl.
| | | |
|---|---|---|
| C08F 2/46 | (2006.01) | |
| C08F 2/50 | (2006.01) | |
| C08G 61/04 | (2006.01) | |
| A61K 6/887 | (2020.01) | |
| A61K 6/62 | (2020.01) | |
| C08F 222/10 | (2006.01) | |
| C08F 220/30 | (2006.01) | |
| C08F 220/18 | (2006.01) | |
| A61C 13/00 | (2006.01) | |
| C08F 220/20 | (2006.01) | |
| C08K 5/5397 | (2006.01) | |
| B33Y 10/00 | (2015.01) | |
| B33Y 70/00 | (2020.01) | |
| B33Y 80/00 | (2015.01) | |

(52) U.S. Cl.
CPC ............ *C08F 2/50* (2013.01); *A61C 13/0019* (2013.01); *A61K 6/62* (2020.01); *A61K 6/887* (2020.01); *C08F 220/1811* (2020.02); *C08F 220/20* (2013.01); *C08F 220/301* (2020.02); *C08F 222/1065* (2020.02); *C08K 5/5397* (2013.01); *B33Y 10/00* (2014.12); *B33Y 70/00* (2014.12); *B33Y 80/00* (2014.12)

(58) Field of Classification Search
CPC ............ C08K 5/5397; C08F 220/1811; C08F 220/20; C08F 220/301; C08F 222/1065; B33Y 10/00; B33Y 80/00; B33Y 70/00; A61K 6/62; A61K 6/887
USPC ........... 522/38, 33, 6, 189, 184, 71, 1; 520/1
See application file for complete search history.

(56) References Cited

U.S. PATENT DOCUMENTS

| | | | | |
|---|---|---|---|---|
| 2012/0296061 A1* | 11/2012 | Naruse | ................. | C08G 18/758 560/115 |
| 2018/0110683 A1* | 4/2018 | Yoshinaga | ............ | C07C 271/20 |
| 2022/0153894 A1* | 5/2022 | Sakamaki | ......... | C08F 222/1065 |

FOREIGN PATENT DOCUMENTS

| | | | |
|---|---|---|---|
| JP | 2016525150 A | | 8/2016 |
| JP | 2019199448 | * | 11/2019 |
| JP | 2019199448 A | | 11/2019 |
| WO | 2014172716 A1 | | 10/2014 |

OTHER PUBLICATIONS

Ito et al, JP 2019-199448 Machine Translation, Nov. 21, 2019 (Year: 2019).*

* cited by examiner

*Primary Examiner* — Jessica Whiteley
(74) *Attorney, Agent, or Firm* — BUCHANAN INGERSOLL & ROONEY PC

(57) ABSTRACT

A photocurable composition includes a photopolymerizable component and a photopolymerization initiator. When a test piece with 39 mm length, 8 mm width, and 4 mm thickness, is produced by photofabrication under conditions in which the photocurable composition is irradiated with visible light having 405 nm wavelength at 12 mJ/cm² irradiation dose to form a cured layer with 100 m thickness, the cured layer is stacked in a thickness direction thereof to form a rectangular fabrication product with 39 mm length, 8 mm width, and 4 mm thickness, and the fabrication product is irradiated with ultraviolet rays having 365 nm wavelength at 10 J/cm² irradiation dose to produce the test piece, a total fracture work of the test piece measured in compliance with ISO20795-1:2008 is 1100 J/m² or more.

17 Claims, No Drawings

PHOTOCURABLE COMPOSITION, CURED PRODUCT, AND DENTAL PRODUCT

TECHNICAL FIELD

The present disclosure relates to a photocurable composition, a cured product, and a dental product.

BACKGROUND ART

In recent years, photocurable compositions have been used as raw materials for obtaining three-dimensional photofabrication products (i.e., cured products obtained by photofabrication) by using 3D printers and the like.

Photofabrication products obtained by using the photocurable compositions are used for various applications, including dental products.

For example, Patent Document 1 discloses a composition that can be used for photofabrication of denture bases and artificial teeth, and a composition containing a urethane dimethacrylate, diethylene glycol dimethacrylate, and the like in the Example of Patent Document 1.

Patent Document 1: Japanese National-Phase Publication (JP-A) No. 2016-525150

SUMMARY OF INVENTION

Technical Problem

By the way, in the case of using a cured product (for example, a photofabrication product) of a photocurable composition as at least a portion of a dental product (for example, medical device used in an oral cavity (for example, a partial denture)), the aforementioned cured product may crack when the dental product is fitted into the oral cavity.

Therefore, crack resistance (i.e., resistance to cracking) may be required for the cured product of the photocurable composition used as the dental product.

Moreover, crack resistance may also be required for a cured product of a photocurable composition used for applications other than the dental product.

An object of an aspect of the present disclosure is to provide a photocurable composition capable of producing a cured product excellent in crack resistance (i.e., resistance to cracking) as well as a cured product excellent in crack resistance and a dental product excellent in crack resistance.

The means to solve the aforementioned problems includes the following aspects.

<1> A photocurable composition comprising a photopolymerizable component and a photopolymerization initiator, wherein:
in a case in which a test piece P1 with a length of 39 mm, a width of 8 mm, and a thickness of 4 mm, is produced by photofabrication under conditions in which the photocurable composition is irradiated with visible light having a wavelength of 405 nm at an irradiation dose of 12 mJ/cm$^2$ to form a cured layer P1 with a thickness of 100 µm, the cured layer P1 is stacked in a thickness direction thereof to form a rectangular fabrication product P1 with a length of 39 mm, a width of 8 mm, and a thickness of 4 mm, and the fabrication product P1 is irradiated with ultraviolet rays having a wavelength of 365 nm at an irradiation dose of 10 J/cm$^2$ to produce the test piece P1, a total fracture work of the test piece P1 measured in compliance with ISO20795-1:2008 is 1100 J/m$^2$ or more.

<2> The photocurable composition according to <1>, wherein:
in a case in which a test piece P2 with a length of 64 mm, a width of 10 mm, and a thickness of 3.3 mm, is produced by photofabrication under conditions in which the photocurable composition is irradiated with visible light having a wavelength of 405 nm at an irradiation dose of 12 mJ/cm$^2$ to form a cured layer P2 with a thickness of 100 µm, the cured layer P2 is stacked in a thickness direction thereof to form a rectangular fabrication product P2 with a length of 64 mm, a width of 10 mm, and a thickness of 3.3 mm, and the fabrication product P2 is irradiated with ultraviolet rays having a wavelength of 365 nm at an irradiation dose of 10 J/cm$^2$ to produce the test piece P2, a flexural modulus of the test piece P2 measured in compliance with ISO20795-1:2008 is 2,500 MPa or less.

<3> The photocurable composition according to <1> or <2>, wherein
in a case in which a test piece P2 with a length of 64 mm, a width of 10 mm, and a thickness of 3.3 mm, is produced by photofabrication under conditions in which the photocurable composition is irradiated with visible light having a wavelength of 405 nm at an irradiation dose of 12 mJ/cm$^2$ to form a cured layer P2 with a thickness of 100 µm, the cured layer P2 is stacked in a thickness direction thereof to form a rectangular fabrication product P2 with a length of 64 mm, a width of 10 mm, and a thickness of 3.3 mm, and the fabrication product P2 is irradiated with ultraviolet rays having a wavelength of 365 nm at an irradiation dose of 10 J/cm$^2$ to produce the test piece P2, a flexural strength of the test piece P2 measured in compliance with ISO20795-1:2008 is 70 MPa or less.

<4> The photocurable composition according to any one of <1> to <3>, wherein the photopolymerizable component comprises:
a di(meth)acrylic monomer (A) having two (meth)acryloyloxy groups and two urethane bonds; and
an acrylic monomer (B) having one acryloyl group.

<5> The photocurable composition according to <4>, wherein a proportion of a number of acryloyl groups with respect to a total number of acryloyl groups and methacryloyl groups in the photocurable composition is 40% or more.

<6> The photocurable composition according to <4> or <5>, wherein di(meth)acrylic monomer (A) comprises a compound represented by the following Formula (1),

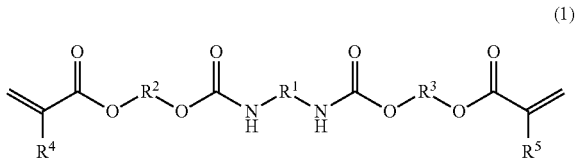

(1)

wherein, in Formula (1), R$^1$ is a divalent chain hydrocarbon group, a divalent hydrocarbon group with an aromatic structure, or a divalent hydrocarbon group with an alicyclic structure; each of R$^2$ and R$^3$ is independently a divalent chain hydrocarbon group that may have a substituent; and each of R$^4$ and R$^5$ is independently a methyl group or a hydrogen atom.

<7> The photocurable composition according to <6>, wherein, in Formula (1):
$R^1$ is a divalent hydrocarbon group with an aromatic structure, having from 6 to 12 carbon atoms, or a divalent hydrocarbon group with an alicyclic structure, having from 6 to 12 carbon atoms; and
each of $R^2$ and $R^3$ is independently a divalent chain hydrocarbon group having from 2 to 6 carbon atoms and no substituent.
<8> The photocurable composition according to any one of <4> to <7>, wherein the acrylic monomer (B) comprises at least one of a compound represented by the following Formula (2) or a compound represented by the following Formula (3),

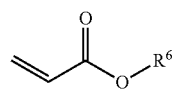

(2)

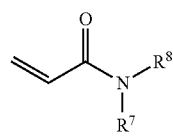

(3)

wherein, in Formula (2), $R^6$ is a monovalent organic group that may have a ring structure, and
wherein, in Formula (3), each of $R^7$ and $R^8$ is independently a hydrogen atom or a monovalent organic group that may have a ring structure, and $R^7$ and $R^8$ may form a ring by bonding with each other.
<9> The photocurable composition according to <8>, wherein:
the acrylic monomer (B) comprises the compound represented by Formula (2); and
in Formula (2), $R^6$ is a monovalent organic group with a ring structure, having from 6 to 20 carbon atoms.
<10> The photocurable composition according to any one of <4> to <9>, wherein a weight-average molecular weight of the di(meth)acrylic monomer (A) is from 380 to 4,000.
<11> The photocurable composition according to any one of <4> to <10>, wherein a weight-average molecular weight of the acrylic monomer (B) is from 130 to 320.
<12> The photocurable composition according to any one of <4> to <11>, wherein a content of the di(meth)acrylic monomer (A) is from 200 parts by mass to 850 parts by mass with respect to 1000 parts by mass of a total content of (meth)acrylic monomer components comprised in the photocurable composition.
<13> The photocurable composition according to any one of <4> to <12>, wherein a total content of the di(meth)acrylic monomer (A) and the acrylic monomer (B) is 800 parts by mass or more with respect to 1000 parts by mass of a total content of (meth)acrylic monomer components comprised in the photocurable composition.
<14> The photocurable composition according to any of <1> to <13>, having a viscosity of from 20 mPa·s to 5000 mPa·s, measured with an E-type viscometer under conditions of 25° C. and 50 rpm.
<15> The photocurable composition according to any one of <1> to <14>, which is a photocurable composition for photofabrication.
<16> A cured product of the photocurable composition according to any one of <1> to <15>.
<17> A dental product comprising the cured product according to <16>.
<18> The dental product according to <17>, which is a medical device used in an oral cavity.

Advantageous Effects of Invention

According to an aspect of the present disclosure, a photocurable composition capable of producing a cured product excellent in crack resistance (i.e., resistance to cracking) as well as a cured product excellent in crack resistance and a dental product excellent in crack resistance.

DESCRIPTION OF EMBODIMENTS

In the present disclosure, the range of numerical values expressed by using "~" refers to a range including the numerical values described before and after "~" as lower limits and upper limits.

In the disclosure, in a case in which a plurality of substances corresponding to each component is present in a composition, the amount of each component contained in the composition refers to a total amount of the plurality of substances present in the composition, unless otherwise specified.

In the ranges of numerical values described stepwise herein, the upper limit or lower limit described in one range of numerical values may be replaced by the upper limit or lower limit of other range of numerical values described stepwise. Moreover, in the ranges of numerical values described in the disclosure, the upper limits or lower limits of the ranges of numerical values may be replaced by the values shown in Examples.

In the disclosure, "light" is a concept that encompasses active energy rays such as ultraviolet light and visible light.

In the present disclosure, "(meth)acrylate" refers to an acrylate or a methacrylate, "(meth)acryloyl" refers to acryloyl or methacryloyl, and "(meth)acrylic" refers to acrylic or methacrylic.

[Photocurable Composition]

The photocurable composition of the present disclosure is a photocurable composition including a photopolymerizable component and a photopolymerization initiator, wherein: in a case in which a test piece P1 with a length of 39 mm, a width of 8 mm, and a thickness of 4 mm, is produced by photofabrication under conditions in which the photocurable composition is irradiated with visible light having a wavelength of 405 nm at an irradiation dose of 12 mJ/cm² to form a cured layer P1 with a thickness of 100 μm, the cured layer P1 is stacked in a thickness direction thereof to form a rectangular fabrication product P1 with a length of 39 mm, a width of 8 mm, and a thickness of 4 mm, and the fabrication product P1 is irradiated with ultraviolet rays having a wavelength of 365 nm at an irradiation dose of 10 J/cm² to produce the test piece P1, a total fracture work of the test piece P1 measured in compliance with ISO20795-1:2008 is 1100 J/m² or more.

According to the photocurable composition of the disclosure, the total fracture work of test piece P1 is 1100 J/m² or more, enabling a cured product excellent in crack resistance (i.e., resistance to cracking) to be produced.

Here, the producing conditions upon producing the cured product by using the photocurable composition of the disclosure are not particularly limited and are not necessarily the same as those of fabricating test piece P1. Even in a case in which the producing conditions of the cured product and the producing conditions of test piece P1 differ from each other, there is a correlation between the total fracture work of test piece P1 and the crack resistance of the cured product. Namely, the total fracture work of test piece P1 is an indicator of the crack resistance of the cured product produced by using the photocurable composition of the disclosure.

The method for producing the cured product by using the photocurable composition of the disclosure is preferably photofabrication. In this case, the correlation between the total fracture work of test piece P1 and the crack resistance of the cured product becomes stronger, thereby achieving more effectively the effect of the photocurable composition of the disclosure (i.e., the effect of improving the crack resistance of the cured product).

Namely, the photocurable composition of the disclosure is preferably a photocurable composition for photofabrication, in other words, the cured product produced by using the photocurable composition of the disclosure is preferably a photofabrication product (namely, a cured product by photofabrication).

The photofabrication is a method for repeatedly forming cured layers by irradiating light onto a photocurable composition and stacking the cured layers to obtain a cured product (i.e., a photofabrication product).

The photofabrication may be photofabrication by an inkjet method or photofabrication by a liquid bath method (i.e., photofabrication using a liquid bath).

From the viewpoint of more effectively achieving the effect of the photocurable composition of the disclosure, the liquid bath method is preferably used for the photofabrication.

In the photofabrication by the inkjet method, droplets of the photocurable composition are ejected from an inkjet nozzle onto a substrate, and the droplets adhering to the substrate are irradiated with light to obtain a cured product.

In one example of photofabrication by the inkjet method, for example, while scanning a head provided with an inkjet nozzle and a light source in a plane, a photocurable composition is ejected from the inkjet nozzle onto a substrate, and the ejected photocurable composition is irradiated with light to form a cured layer, and these operations are repeated to form cured layers in sequence then to obtain a cured product (i.e., a photofabrication product).

In the photofabrication by the liquid bath method, a portion of a photocurable composition housed in a liquid bath (i.e., an uncured photocurable composition in a liquid state. The same applies hereinafter.) is irradiated by light and cured to form a cured layer, and these operations are repeated to stack the cured layers and then to obtain a cured product (i.e., a photofabrication product). The photofabrication by the liquid bath method differs from that by the inkjet method in that the former uses a liquid bath.

Examples of the photofabrication by the liquid bath include photofabrication by a DLP (Digital Light Processing) method and photofabrication by an SLA (Stereolithography) method.

In the DLP method, planar light is irradiated onto the photocurable composition in the liquid bath.

In the SLA method, a laser beam is scanned onto the photocurable composition in the liquid bath.

From the viewpoint of more effectively achieving the effect of the photocurable composition of the disclosure, the DLP method is preferably used as the photofabrication by the liquid bath method.

In one example of photofabrication by the DLP method, for example, a 3D printer (for example, a "Cara Print4.0" manufactured by Kulzer GmbH, or a "Max UV" manufactured by Asiga GmbH, etc.) comprising:
a build table that can be moved in the vertical direction;
a tray (i.e., liquid bath) arranged below the build table (on a side in the gravity direction. The same applies hereinafter.), including a light transmissive portion and housing a photocurable composition; and
a light source (for example, an LED light source) arranged below the tray for irradiating the photocurable composition in the tray with planar light through the light transmissive portion of the tray, is used.

In this example, first, a gap of one layer is arranged between the build table and the tray, and this gap is filled with the photocurable composition. Next, the photocurable composition filled in the gap is irradiated with planar light from below through the light transmissive portion of the tray to cure the area irradiated by the light and to form a first cured layer. Next, the gap between the build table and the tray is widened by one layer for the next layer, and the space created is filled with a photocurable composition. Subsequently, the photocurable composition filled in the space is irradiated in the same manner as the first layer to form a cured second cured layer. By repeating the above operations, the cured layers are stacked to produce a three-dimensional photofabrication product. In this example, the three-dimensional product produced may be further cured by further irradiation with light.

For the photofabrication by the DLP method, the description of Japanese Patent Publication (JP-B) No. 5111880 and JP-B No. 5235056 may be referred to.

<Applications>

The applications of the photocurable composition of the disclosure are not particularly limited.

The photocurable composition of the disclosure is preferably a photocurable composition used for producing a dental product from the viewpoint of more effectively exhibiting the effect of crack resistance of the cured film.

The dental products include dental prosthetics, medical device used in an oral cavity, dental models, patterns for evaporative casting, and the like.

The dental prosthetics include inlays, crowns, bridges, temporary crowns, temporary bridges, and the like.

The medical device used in an oral cavity includes dentures (for example, complete dentures, partial dentures, etc.), mouthpieces, mouthguards, orthodontic appliances, occlusal splints, impression trays, surgical guides, and the like.

Examples of the dental model include a dentognathic model, and the like.

In the case of producing at least a portion of medical device (for example, a partial denture) to be used in an oral cavity as the cured product of the photocurable composition of the disclosure, the effect of improving the crack resistance of the cured product is particularly effectively demonstrated. In this case, cracks of the cured product above are effectively inhibited upon fitting the medical device above into an oral cavity.

<Total Fracture Work of Test Piece P1>

As described above, the total fracture work of test piece P1 prepared by using the photocurable composition of the disclosure is 1100 J/m$^2$ or more.

The total fracture work of test piece P1 is preferably 1200 J/m² or more and more preferably 3000 J/m² or more from the viewpoint of being more excellent in the crack resistance (resistance to cracking) of the cured product of the photocurable composition of the disclosure.

The upper limit of the total fracture work of test piece P1 is not particularly limited, and includes, for example, 20,000 J/m² with 11,000 J/m² being preferred.

(Test Piece P1)

A test piece P1 is a rectangular test piece with a length of 39 mm, a width of 8 mm, and a thickness of 4 mm.

Test piece P1 was produced by photofabrication under the conditions of irradiating the photocurable composition of the disclosure with a visible light of wavelength of 405 nm at an irradiation dose of 12 mJ/cm² to form a cured layer P1 with a thickness of 100 μm, and stacking cured layer P1 in the thickness direction thereof to form a rectangular fabrication product P1 with a length of 39 mm, a width of 8 mm, and a thickness of 4 mm, and irradiating fabrication product P1 with ultraviolet rays of wavelength of 365 nm at a dose of 10 J/cm².

Test piece P1 can be produced, for example, according to an example of the photofabrication by the DLP method described above.

In Examples described below, the "Cara Print4.0" manufactured by Kulzer GmbH, which is a 3D printer by the DLP method was used to fabricate test piece P1.

(Total Fracture Work)

The total fracture work of test piece P1 is measured in complied with ISO 20795-1:2008.

Specifically, test piece P1 is applied to notch processing complied with ISO 20795-1:2008, and then stored in a thermostatic water bath at 37±1° C. for 7 days±2 hours.

Thereafter, test piece P1 is removed from the thermostatic bath, and the removed test piece P1 is subjected to a fracture toughness test by a flexural test complied with ISO 20795-1:2008 to determine the total fracture work (J/m²).

The fracture toughness test by a flexural test (i.e., measurement of total fracture work) is carried out by using a universal testing machine at an indentation speed of 1.0±0.2 mm/min.

In Examples described below, a universal testing machine manufactured by INTESCO Co., Ltd., was used as the universal testing machine.

<Flexural Modulus of Test Piece P2>

In a case in which a test piece P2 with a length of 64 mm, a width of 10 mm, and a thickness of 3.3 mm, is produced by photofabrication under conditions in which the photocurable composition is irradiated with visible light having a wavelength of 405 nm at an irradiation dose of 12 mJ/cm² to form a cured layer P2 with a thickness of 100 μm, the cured layer P2 is stacked in a thickness direction thereof to form a rectangular fabrication product P2 with a length of 64 mm, a width of 10 mm, and a thickness of 3.3 mm, and the fabrication product P2 is irradiated with ultraviolet rays having a wavelength of 365 nm at an irradiation dose of 10 J/cm² to produce the test piece P2, a flexural modulus of the test piece P2 measured in compliance with ISO20795-1:2008 is preferably 2,500 MPa or less.

Test piece P2 having a flexural modulus of 2,500 MPa or less reduces the flexural modulus of the cured product produced by using the photocurable composition of the disclosure, thereby further improving usability of the cured product.

For example, in the case of producing at least a portion of medical device (for example, a partial denture) to be used in an oral cavity as the cured product of the photocurable composition of the disclosure, it is more excellent in usability upon fitting the medical device in the oral cavity (for example, it is less likely to cause pain in the oral cavity).

The flexural modulus of test piece P2 is more preferably 2,400 MPa or less, and more preferably 2,000 MPa or less.

The lower limit of the flexural modulus of test piece P2 is not particularly limited, and is preferably 30 MPa, and 200 MPa from the viewpoint of a cured product.

Here, the producing conditions upon production of the cured product by using the photocurable composition of the disclosure are not necessarily the same as those of fabricating test piece P2. Even in a case in which the producing conditions of the cured product and the producing conditions of test piece P2 differ from each other, there is a correlation between the flexural modulus of test piece P2 and the flexural modulus of the cured product.

Namely, the flexural modulus of test piece P2 is an index of the flexural modulus of the cured product produced by using the photocurable composition of the disclosure.

(Test Piece P2)

Test piece P2 can be produced, for example, according to one example of the photofabrication by the DLP method described above.

In Examples described below, test piece P2 was produced by using the "Cara Print4.0" manufactured by Kulzer GmbH, which is a 3D printer by the DLP method.

(Flexural Modulus)

The flexural modulus of test piece P2 is measured as follows:

Test piece P2 is stored in a thermostatic bath at 37±1° C. for 50±2 hours.

Thereafter, test piece P2 is removed from the thermostatic bath, and the flexural modulus of test piece P2 removed is determined under the conditions of a test rate of 5±1 mm/min, complied with ISO 20795-1:2008.

In Examples described below, a universal testing machine (manufactured by INTESCO Co., Ltd.) was used as the measurement apparatus for the flexural modulus.

<Flexural Strength of Test Piece P2>

In a case in which the test piece P2 is produced by using the photocurable composition of the disclosure, a flexural strength of of the test piece P2 measured complied with ISO2095-1:2008 is preferably 70 MPa or less.

Test piece P2 having the flexural strength of 70 MPa or less reduces the flexural modulus of the cured product produced by using the photocurable composition of the disclosure, thereby further improving usability of the cured product.

For example, in the case of producing at least a portion of medical device (for example, a partial denture) to be used in an oral cavity as the cured product of the photocurable composition of the disclosure, it is more excellent in usability upon fitting the medical device in an oral cavity (for example, it is less likely to cause pain in the oral cavity).

The flexural strength of test piece P2 is more preferably 60 MPa or less.

The lower limit of the flexural modulus of test piece P2 is not particularly limited and is preferably 2 MPa and more preferably 10 MPa from the viewpoint of the cured product.

Here, the producing conditions upon production of the cured product by using the photocurable composition of the disclosure are not necessarily the same as those of fabricating test piece P2. Even in a case in which the producing conditions of the cured product and the producing conditions of test piece P2 differ from each other, there is a correlation between the flexural strength of test piece P2 and the flexural strength of the cured product.

Namely, the flexural strength of test piece P2 is an index of the flexural strength of the cured product produced by using the photocurable composition of the disclosure.

(Flexural Strength)

The flexural strength of test piece P2 is measured as follows:

Test piece P2 is stored in a thermostatic bath at 37±1° C. for 50±2 hours.

Thereafter, test piece P2 is removed from the thermostatic bath, and the flexural strength of test piece P2 removed is determined under the conditions of a test rate of 5±1 mm/min, complied with ISO 20795-1:2008.

In Examples described below, a universal testing machine (manufactured by INTESCO Co., Ltd.) was used as the measurement apparatus for the flexural strength.

<Photopolymerizable Components>

The photocurable composition of the disclosure contains at least one type of a photopolymerizable component.

Examples of the photopolymerizable component include a compound containing an ethylenic double bond.

Examples of the compound containing the ethylenic double bond include a (meth)acrylic monomer, styrene, styrene derivatives, (meth)acrylonitrile, and the like.

A photopolymerizable component that is the photopolymerizable component described in paragraphs from 0030 to 0059 of WO2019/189652 may be used.

From the viewpoint of further improving the crack resistance of the cured product, the content of the photopolymerizable components with respect to the total amount of the photocurable composition of the disclosure is preferably 60% by mass or more, more preferably 80% by mass or more, and still more preferably 90% by mass or more.

The photopolymerizable component preferably contains at least one type of (meth)acrylic monomer.

Here, the (meth)acrylic monomer refers to a monomer having one or more (meth)acryloyl groups in the molecule.

In the present disclosure, all (meth)acrylic monomers contained in the photocurable composition may be referred to as "(meth)acrylic monomer components," and the total content of all (meth)acrylic monomers contained in the photocurable composition of the disclosure may be referred to as a "total content of (meth)acrylic monomer components."

From the viewpoint of further improving the crack resistance of the cured product, the total content of (meth)acrylic monomer components with respect to the total amount of the photopolymerizable components in the photocurable composition of the disclosure is preferably 80% by mass or more, more preferably 90% by mass or more, and still more preferably 95% by mass or more.

From the viewpoint of further improving the crack resistance of the cured product, the total content of the (meth)acrylic monomer components with respect to the total amount of the photocurable composition of the present disclosure, is preferably 60% by mas or more, more preferably 80% by mass or more, and still more preferably 90% by mass or more.

The (meth)acrylic monomer constituting the (meth)acrylic monomer component may be any monomer having one or more (meth)acryloyl groups in the molecule, and otherwise not particularly limited thereto.

The (meth)acrylic monomer may be a monofunctional (meth)acrylic monomer (i.e., a monomer having one (meth)acryloyl group in the molecule), a bifunctional (meth)acrylic monomer (i.e., a monomer having two (meth)acryloyl groups in the molecule), or a multifunctional (meth)acrylic monomer (i.e., a (meth)acrylic monomer of three or more functional groups; i.e., a monomer having three or more (meth)acryloyl groups in the molecule).

The (meth)acrylic monomer preferably includes in the molecule thereof, at least one of an aromatic structure (for example, a bisphenol A structure and the like), an alicyclic structure, or a urethane bond.

The (meth)acrylic monomer according to a preferred aspect may further contain at least one of an ethyleneoxy group or a propyleneoxy group.

The weight-average molecular weight (Mw) of the (meth)acrylic monomer is preferably 5,000 or less, more preferably 3,000 or less, still more preferably 2,000 or less, still more preferably 1,500 or less, still more preferably 1,000 or less, and even still more preferably 800 or less.

The lower limit of Mw of (meth)acrylic monomer is not particularly limited as long as the monomer contains one or more (meth)acryloyl groups in the molecule. The lower limit of Mw of the (meth)acrylic monomer is, for example, 86, and preferably 100.

From the viewpoint of reducing the viscosity of the photocurable composition, the (meth)acrylic monomer component that can be contained in the photocurable composition of the present disclosure preferably contains at least one of a monofunctional (meth)acrylic monomer or a bifunctional (meth)acrylic monomer.

In this case, from the viewpoint of reducing the viscosity of the photocurable composition, the total content of the monofunctional (meth)acrylic monomer and the bifunctional (meth)acrylic monomer with respect to the total amount of (meth)acrylic monomer components that can be contained in the photocurable composition of the disclosure is preferably 60% by mass or more, more preferably 80% by mass or more, and still more preferably 90% by mass or more.

In the photocurable composition of the disclosure, the proportion of the number of acryloyl groups to the total number of acryloyl groups and methacryloyl groups in the photocurable composition (hereinafter simply referred to as "proportion of the number of acryloyl groups") is preferably 10% or more.

The proportion of the number of acryloyl groups of 10% or more enables the crack resistance of the cured product to be further improved.

From the viewpoint of further improving the crack resistance of the cured product, the proportion of the number of acryloyl groups is more preferably 20% or more, still more preferably 30% or more, even still more preferably 40% or more, even furthermore preferably 50% or more, 60% or more, or 70% or more, and particularly preferably 100%.

The photopolymerizable component in the photocurable composition of the disclosure preferably contains at least one of a di(meth)acrylic monomer (A) having two (meth)acryloxy groups and two urethane bonds, or an acrylic monomer (B) having one acryloyl group, and more preferably both di(meth)acrylic monomer (A) and acrylic monomer (B).

In a case in which the photopolymerizable component contains at least one (preferably both) of di(meth)acrylic monomer (A) or acrylic monomer (B), the total fracture work of test piece P1 that is 1,100 $J/m^2$ or more is easily achieved. Furthermore, the flexural modulus of test piece P2 of 2,500 MPa or less and the flexural strength of test piece of P2 of 70 MPa or less, are also likely to be achieved. Furthermore, the reduction in viscosity of the photocurable composition is likely to be achieved as well.

Increase in content of acrylic monomer (B) facilitates improvement on the total fracture work and adjustment of flexural modulus and flexural strength to lower values to be particularly achieved.

(Di(Meth)Acrylic Monomer (A))

Di(meth)acrylic monomer (A) in the disclosure is a compound having two (meth)acryloyloxy groups and two urethane bonds (i.e., a bifunctional urethane (meth)acrylate).

Di(meth)acrylic monomer (A) has no (meth)acryloyloxy group other than the two (meth)acryloyloxy groups. Di(meth)acrylic monomer (A) has no urethane bond other than the two urethane bonds.

The photopolymerizable component in the photocurable composition of the disclosure may contain one type of di(meth)acrylic monomer (A) singly or may contain two or more types thereof.

Di(meth)acrylic monomer (A) preferably contains the compound represented by the following Formula (1).

In this case, the content of the compound represented by the following Formula (1) with respect to the total amount of di(meth)acrylic monomer (A) is preferably 60% by mass or more and more preferably 80% by mass or more.

The content of the compound represented by Formula (1) below with respect to the total amount of di(meth)acrylic monomer (A) may be 100% by mass.

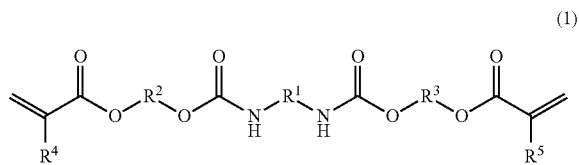

(1)

In Formula (1), $R^1$ is a divalent chain hydrocarbon group, a divalent hydrocarbon group with an aromatic structure, or a divalent hydrocarbon group with an alicyclic structure, each of $R^2$ and $R^3$ is independently a divalent chain hydrocarbon group that may have a substituent, and each of $R^4$ and $R^5$ is independently a methyl group or a hydrogen atom.

In Formula (1), $R^1$ is preferably a divalent hydrocarbon group with an aromatic structure, or a divalent hydrocarbon group with an alicyclic structure.

$R^1$ containing these ring structures more inhibits the viscosity of the photocurable composition. Furthermore, this facilitates the total fracture work of test piece P1 of 1,100 J/m² or more, the flexural modulus of test piece P2 of 2,500 MPa or less, and the flexural strength of test piece P2 of 70 MPa or less to be further achieved.

In $R^1$ in Formula (1), the number of carbon atoms of the divalent chain hydrocarbon group is preferably from 1 to 20, more preferably from 1 to 10, and still more preferably from 2 to 6.

The divalent chain hydrocarbon group in $R^1$ may be linear or branched, saturated or unsaturated, and may have a substituent.

The divalent chain hydrocarbon group in $R^1$ is preferably a linear- or branched-alkylene group having from 1 to 20 carbon atoms, more preferably a linear- or branched-alkylene group having from 1 to 12 carbon atoms, and particularly preferably a linear- or branched-alkylene group having from 1 to 10 carbon atoms.

Specific examples of the linear- or branched-alkylene group having from 1 to 20 carbon atoms include a methylene group, an ethylene group, a propanediyl group, a butanediyl group, a pentanediyl group, a hexanediyl group, a heptanediyl group, an octanediyl group, a nonanediyl group, a decanediyl group, an undecanediyl group, a dodecanediyl group, a tridecanediyl group, a tetradecanediyl group, a pentadecanediyl group, an octadecanediyl group, an eicosylene group, a vinylene group, a propenediyl group, a butenediyl group, a pentendiyl group, an ethynylene group, a propynylene group, a 2,4,4-trimethylhexylene group. Among them, 2,4,4-trimethylhexylene group is particularly preferred.

In $R^1$ of Formula (1), the divalent hydrocarbon group with an aromatic structure is preferably a divalent hydrocarbon group with an aromatic structure, having from 6 to 20 carbon atoms (more preferably from 6 to 12 carbon atoms and still more preferably from 6 to 10 carbon atoms), which may have a substituent.

Examples of the divalent hydrocarbon group with an aromatic structure include an arylene group, an alkylenearylene group, an alkylene-arylene-alkylene group, and an arylene-alkylene-arylene group.

The divalent hydrocarbon group with an aromatic structure is preferably an alkylenearylene group or an alkylene-arylene-alkylene group. This further inhibits the viscosity of the photocurable composition and facilitates the total fracture work of test piece P1 of 1,100 J/m² or more, the flexural modulus of test piece P2 of 2,500 MPa or less, and the flexural strength of test piece P2 of 70 MPa or less to be achieved.

Specific examples of the arylene group, the alkylenearylene group, the alkylene-arylene-alkylene group, an alkylarylene group, and the arylene-alkylene-arylene group include a 1,3- or 1,4-phenylene group, a 1,3- or 1,4-phenylenedimethylene group, and a 1,3- or 1,4-phenylenedimethylene group.

In $R^1$ of Formula (1), the divalent hydrocarbon group with an alicyclic structure preferably has from 3 to 20 carbon atoms, more preferably from 6 to 12 carbon atoms, and particularly preferably from 6 to 8 carbon atoms.

Examples of the alicyclic structure include a cyclopropylene group, a cyclobutylene group, a cyclopentylene group, a cyclohexylene group, a cyclohexenylene group, a cycloheptylene group, a cyclooctylene group, a cyclononylene group, a cyclodecylene group, a cycloundecylene group, a cyclododecylene group, a cyclotridecylene group, a cyclotetradecylene group, a cyclopentadecylene group, a cyclooctadecylene group, a cycloicosylene group, a bicyclohexylene group, a norbornylene group, an isobornylene group, and an adamantylene group. Among them, the norbornylene group and the isobornylene group are preferred.

In a case in which $R^1$ is a divalent hydrocarbon group with an alicyclic structure, particularly suitable examples are as follows. The symbol * denotes a bonding position.

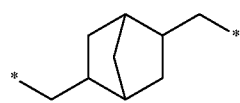 [SMILES: *CC1CC2CC1CC2C*]

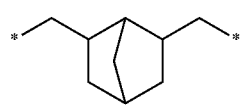 [SMILES: *CC1CC2CC(C*)C1C2]

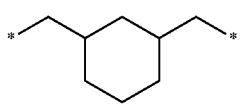 [SMILES: *CC1CCCC(C*)C1]

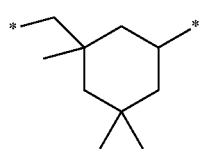 [SMILES: *CC1(C)CC(*)CC(C)(C)C1]

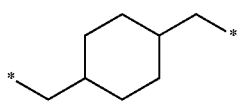 [SMILES: *CC1CCC(C*)CC1]

The divalent hydrocarbon group with an alicyclic structure in $R^1$ in Formula (1) may have a substituent. The substituent includes a linear- or branched-alkyl group having from 1 to 6 carbon atoms.

In $R^1$ in Formula (1), the divalent hydrocarbon group with an alicyclic structure is preferably a divalent hydrocarbon group with a structure bonded to the alicyclic structure via one atomic bonding of each of two alkylene groups (for example, alkylene groups having from 1 to 3 carbon atoms), which may be the same or different (namely, it has a structure in which an alicyclic structure is bonded between two divalent alkylene groups), or a divalent hydrocarbon group with a structure bonded with an alicyclic structure via one atomic bonding of one alkylene group (for example, an alkylene group having from 1 to 3 carbon atoms) and more preferably a divalent hydrocarbon group with a structure in which an alicyclic structure is arranged between two methylene groups, or a divalent hydrocarbon group with a structure in which one methylene group and an alicyclic structure are bonded with each other.

In Formula (1), each of $R^2$ and $R^3$ is independently a divalent chain hydrocarbon group that may have a substituent.

The divalent chain hydrocarbon groups suitable as $R^2$ and $R^3$ are the same as the divalent chain hydrocarbon groups suitable as $R^1$.

However, the divalent chain hydrocarbon group in $R^2$ and $R^3$, which may have a substituent, preferably has the number of carbon atoms from 2 to 6 and more preferably 2 or 3.

In a case in which $R^2$ and $R^3$ are the divalent chain hydrocarbon groups having a substituent, examples of the substituent described above include,
an alkyl group having from 1 to 6 carbon atoms, such as a methyl group or an ethyl group; an aryl group;
a cycloalkyl group having from 3 to 6 carbon atoms, such as a cyclopentyl group or cyclohexyl group;
a tolyl group;
a xylyl group;
a cumyl group;
a styryl group,
an alkoxyphenyl group such as a methoxyphenyl group, an ethoxyphenyl group, or a propoxyphenyl group; and
the like.

From the viewpoint of further inhibiting the viscosity of the photocurable composition, each of $R^2$ and $R^3$ is independently a divalent chain hydrocarbon group having from 2 to 6 carbon atoms (more preferably from 2 to 3 carbon atoms), which has no substituent.

Examples of suitable compounds as di(meth)acrylic monomer (A) include a urethane diacrylate that is a reaction product of one isocyanate selected from the group consisting of, for example, m-xylylene diisocyanate, tetramethylxylylene diisocyanate, norbornene diisocynanate, and isophorone diisocyanate, and one hydroxyacrylate selected from the group consisting of hydroxyethyl acrylate, hydroxypropyl acrylate and 4-hydroxybutyl acrylate.

Examples of di(meth)acrylic monomer (A) also include compounds used in Examples described below.

The weight-average molecular weight (Mw) of di(meth)acrylic monomer (A) is preferably from 380 to 5,000, more preferred from 380 to 4,000, preferably from 380 to 700, and still more preferably from 400 to 650.

Di(meth)acrylic monomer (A) may be synthesized from a monomer commercially available. For example, di(meth)acrylic monomer (A) may be synthesized from two molecules of hydroxy(meth)acrylates and one molecule of a diisocyanate.

Examples of a suitable hydroxy(meth)acrylate are as shown below. Among the following structures, "Et" denotes an ethyl group.

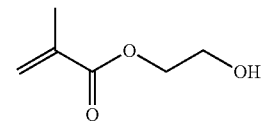

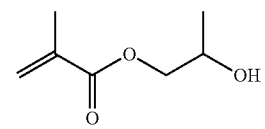

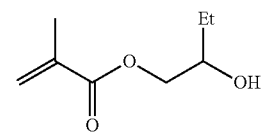

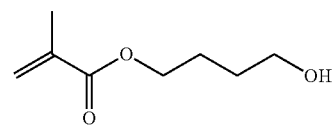

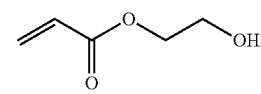

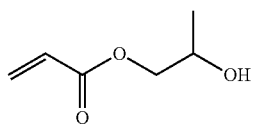
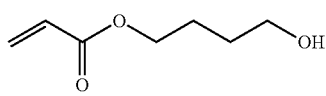
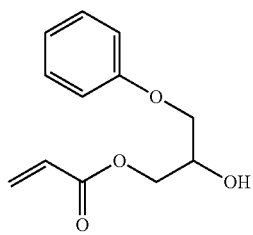 [SMILES: C=CC(=O)OCC(O)COc1ccccc1]
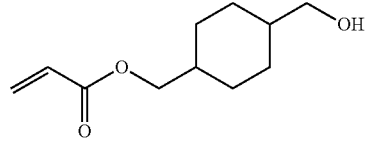
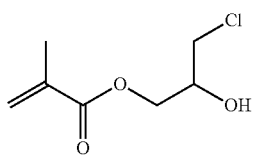
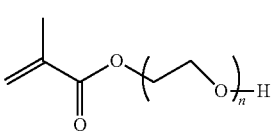
n ≈ 2, 4.5
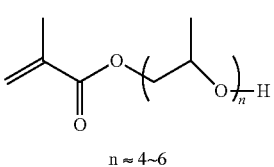
n ≈ 4~6
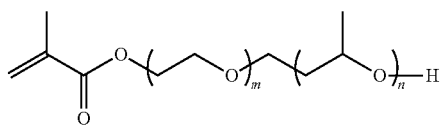
m ≈ 3.5 n ≈ 2.5
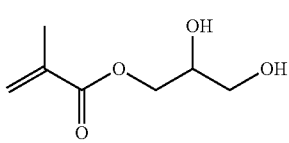
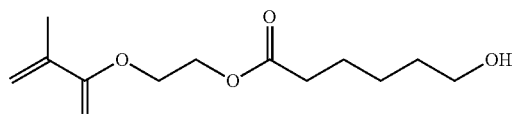
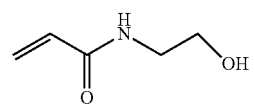
Examples of suitable diisocyanates are as shown below. Among the following structures, "Me" denotes a methyl group.
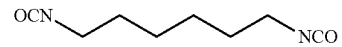
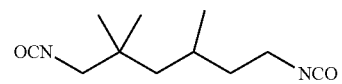
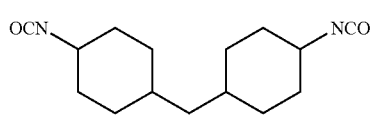

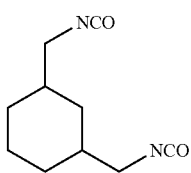

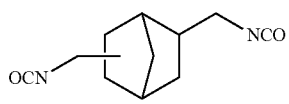

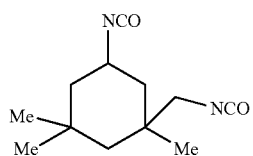

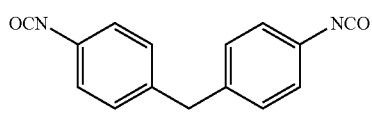

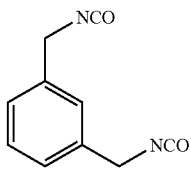

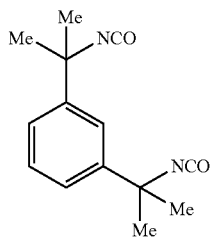

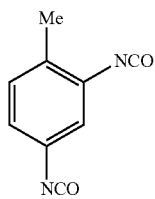

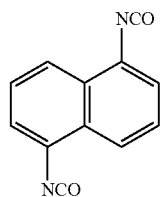

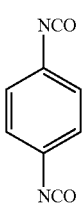

(Acrylic Monomer (B) Having One Acryloyl Group)

Acrylic monomer (B) in the disclosure is a monomer having one acryloyl group (i.e., a monofunctional acrylate).

Acrylic monomer (B) has no acryloyl group other than one acryloyl group. Acrylic monomer (B) preferably has no methacryloyl group.

The photopolymerizable component in the photocurable composition of the disclosure may contain one type of acrylic monomer (B) singly or two or more thereof.

Acrylic monomer (B) preferably contains at least one of the compound represented by the following Formula (2) or the compound represented by the following Formula (3).

In this case, the total content of the compound represented by the following Formula (2) and the compound represented by the following Formula (3) with respect to the total amount of acrylic monomer (B) is preferably 60% by mass or more and more preferably 80% by mass or more.

The total content of the compound represented by the following Formula (2) and the compound represented by the following Formula (3) with respect to the total amount of acrylic monomer (B) may be 100% by mass.

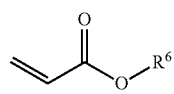

(2)

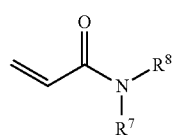

(3)

In Formula (2), $R^6$ is a monovalent organic group that may have a ring structure.

In Formula (3), each of $R^7$ and $R^8$ is independently a monovalent organic group that may have a ring structure, or a hydrogen atom, and $R^7$ and $R^8$ may be bonded together to form a ring.

Acrylic Monomer (B) Preferably Contains the Compound Represented by Formula (2).

$R^6$ in Formula (2) is preferably a monovalent organic group with a ring structure, having from 3 to 30 carbon atoms and more preferable a monovalent organic group with a ring structure, having from 6 to 20 carbon atoms.

In a case in which acrylic monomer (B) contains the compound represented by Formula (2), it is advantageous from the viewpoint of improving the hydrophobicity (i.e., reduction of water absorption) of the cured product.

In a case in which acrylic monomer (B) contains the compound represented by Formula (2), the content of the compound represented by the following Formula (2) with respect to the total amount of acrylic monomer (B) is preferably 60% by mass or more and more preferably 80% by mass or more.

The content of the compound represented by the following Formula (2) with respect to the total amount of acrylic monomer (B) may be 100% by mass.

In Formula (2), $R^6$ may be the organic group represented by Formula (4) below.

(4)

In Formula (4), Li is a single bond or a divalent chain hydrocarbon group having from 1 to 30 carbon atoms, which may have a heteroatom that is O or N. A is a hydrogen atom, a monovalent alicyclic group having from 3 to 30 carbon atoms, which may have a heteroatom that is O or N, or an aryl group having from 6 to 30 carbon atoms. * denotes a bonding position.

In Formula (4), the divalent chain hydrocarbon group represented by Li having from 1 to 30 carbon atoms, which may have a heteroatom that is O or N may be linear or branched.

The divalent chain hydrocarbon group represented by Li having from 1 to 30 carbon atoms, which may have a heteroatom that is O or N preferably has the number of carbon atoms from 1 to 20, more preferably from 1 to 10, and still more preferably from 1 to 8.

In a case in which the divalent chain hydrocarbon group represented by Li contains a heteroatom, the number of heteroatoms in Li is preferably from 1 to 3 and more preferably 1 or 2.

The divalent chain hydrocarbon group represented by Li above may have a substituent.

Suitable examples of the substituent include an alkyl group having from 1 to 3 carbon atoms, a hydroxy group, and an alkyl group having from 1 to 3 carbon atoms in which 1 or 2 of the hydrogen atoms are substituted with a hydroxy group.

The divalent chain hydrocarbon group represented by Li above may contain a urethane bond. In a case in which the divalent chain hydrocarbon group represented by Li above contains a urethane bond, the number of urethane bonds in Li may be 1 or 2.

Specific examples of the divalent chain hydrocarbon group represented by Li in Formula (4) above include the following groups. In the following groups, * denotes a bonding position.

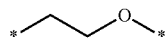

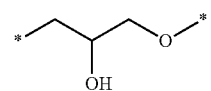 [SMILES: *CC(O)CO*]

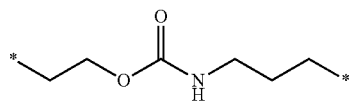 [SMILES: *CCCNC(=O)OCC*]

In Formula (4), specific examples of the monovalent alicyclic group represented by A having from 3 to 20 carbon atoms, which may have a heteroatom that is O or N include a cyclopropyl group, a cyclobutyl group, a cyclopentyl group, a cyclohexyl group, a cyclohexenyl group, a cycloheptyl group, a cyclooctyl group, a cyclononyl group, a cyclodecyl group, a cycloundecyl group, a cyclododecyl group, a cyclotridecyl group, a cyclotetradecyl group, a cyclopentadecyl group, a cyclooctadecyl group, a cycloicosyl group, a bicyclohexyl group, a norbornyl group, an isobornyl group, an adamantyl group, a morphoryl group, a piperidino group, a piperazino group, and a dioxane group.

The monovalent alicyclic group represented by A above preferably has from 5 to 12 carbon atoms and more preferably from 6 to 10 carbon atoms.

In Formula (4), examples of an aromatic structure in the aryl group represented by A having from 6 to 30 carbon atoms include a phenyl structure, a biphenyl structure, a naphthyl structure, and an anthryl structure.

The group represented by A in Formula (4) may have a substituent.

Suitable examples of the substituent above include an alkyl group having from 1 to 6 carbon atoms, such as a methyl group or an ethyl group;

a hydroxy group;

an alkyl group having from 1 to 6 carbon atoms, substituted with one or two hydroxy groups;

an aryl group;

a cycloalkyl group having from 3 to 6 carbon atoms, such as a cyclopentyl group or a cyclohexyl group;

a tolyl group;

a xylyl group;

a cumyl group;

a styryl group;

an alkoxyphenyl group such as a methoxyphenyl group, an ethoxyphenyl group, or a propoxyphenyl group, and the like.

Examples of the group represented by A in Formula (4) include the following examples. * denotes a bonding position.

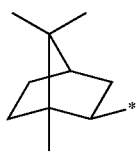 [SMILES: *C1CC2CCC1(C)C2(C)C]

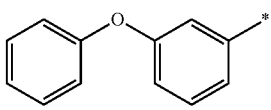 [SMILES: *c1cccc(Oc2ccccc2)c1]

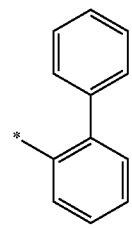 [SMILES: *c1ccccc1-c1ccccc1]

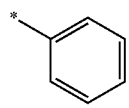

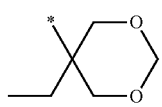

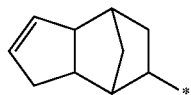 [SMILES: *C1CC2CC1C1CC=CC21]

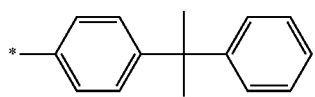 [SMILES: *c1ccc(C(C)(C)c2ccccc2)cc1]

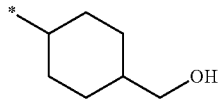 [SMILES: *C1CCC(CO)CC1]

The organic group represented by Formula (4) preferably has the number of carbon atoms from 1 to 30 and more preferably from 1 to 20.

In Formula (3), each of $R^7$ and $R^8$ is independently a monovalent organic group that may have a ring structure or a hydrogen atom, and $R^7$ and $R^8$ may be bonded together to form a ring.

Each of $R^7$ and $R^8$ is independently a monovalent chain hydrocarbon group having from 1 to 30 carbon atoms, which may have a heteroatom that is O or N.

The monovalent chain hydrocarbon group above may be linear or branched, saturated or unsaturated, and may have a substituent.

The monovalent chain hydrocarbon group above preferably has the number of carbon atoms from 1 to 20 and more preferably from 1 to 10.

Examples of an organic group in $R^7$ and $R^8$ include an alkyl group having from 1 to 30 carbon atoms, such as a methyl group, an ethyl group, or a propyl group, which may have a heteroatom that is O or N.

In Formula (2), either one of $R^7$ and $R^8$ is preferably a hydroxyethyl group or a butoxymethyl group, and the other is a hydrogen atom.

Examples of the monomer according to the aspect include monomers shown below.

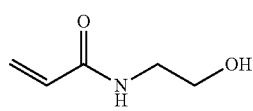

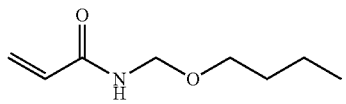

Examples of acrylic monomer (B) in which $R^7$ and $R^8$ are bonded together to form a ring include the following.

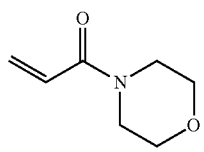

The weight-average molecular weight (Mw) of acrylic monomer (B) is preferably from 80 to 500, more preferably from 100 to 400, and particularly preferably from 130 and 320.

Examples of the suitable compound as acrylic monomer (B) include the compounds used in Examples described below.

The photocurable composition of the disclosure contains di(meth)acrylic monomer (A) preferably in a content from 200 parts by mass to 850 parts by mass, more preferably from 250 parts by mass to 850 parts by mass, and still more preferably from 300 parts by mass to 800 parts by mass, with respect to 1000 parts by mass of the total content of (meth)acrylic monomer components contained in the photocurable composition.

The photocurable composition of the disclosure contains di(meth)acrylic monomer (A) and acrylic monomer (B) in a total content of 800 parts by mass or more, more preferably 900 parts by mass or more, and still more preferably from 950 parts by mass or more, with respect to 1000 parts by mass of the total content of (meth)acrylic monomer components contained in the photocurable composition.

<Photopolymerization Initiator>

The photocurable composition of the disclosure contains at least one type of photopolymerization initiator.

The photopolymerization initiator is not limited as long as it generates radicals by irradiation with light and is preferably an initiator that generates radicals at the wavelength of light used upon photofabrication.

Examples of the wavelength of light used in photofabrication include in general from 365 nm to 500 nm, practically preferably from 365 nm to 430 nm, and more preferably from 365 nm to 420 nm.

Examples of the photopolymerization initiator that generate radicals at the wavelength of light used upon photofabrication include an alkylphenone-based compound, an acylphosphine oxide-based compound, a titanocene-based compound, an oxime ester-based compound, a benzoin-based compound, an acetophenone-based compound, a benzophenone-based compound, a thioxanthone-based compound, an α-acyloxime ester-based compound, a phenylglyoxylate-based compound, a benzyl-based compound, an azo-based compound, a diphenyl sulfide-based compound, an organic dye-based compound, an iron-phthalocyanine-based compound, a benzoin ether-based compound, an anthraquinone-based compound, and the like.

Among them, the alkylphenone-based compound and the acylphosphine-based oxide compound are preferred from the viewpoint of reactivity or the like.

Examples of the alkylphenone-based compound include 1-hydroxy-cyclohexyl-phenyl-ketone (Omnirad 184 manufactured by IGM Resins B.V.).

Examples of the acylphosphine oxide compound include bis(2,4,6-trimethylbenzoyl)-phenylphosphine oxide (Omnirad 819 manufactured by IGM Resins B.V), 2,4,6-trimethylbenzoyl-diphenyl-phosphine oxide (Omnirad TPO manufactured by IGM Resins B.V.).

The photocurable composition of the disclosure may contain one type of photopolymerization initiator singly or two or more types thereof.

The content of the photopolymerization initiator in the photocurable composition of the disclosure (the total content in the case of two or more types thereof) is preferably from 0.1% by mass to 10% by mass, more preferably from 0.2% by mass to 5% by mass, and particularly preferably from 0.3% by mass to 3% by mass.

<Other Components>

The photocurable composition of the disclosure may contain one or more types of other components other than those described above, if necessary.

In a case in which the photocurable composition contains the other component, the total mass of di(meth)acrylic monomer (A), acrylic monomer (B), and the photopolymerization initiator is preferably 30% by mass or more, more preferably 50% by mass or more, still more preferably 70% by mass or more, even still more preferably 80% by mass or more, and even still more preferably 90% by mass or more, with respective to the total amount of the photocurable composition.

Examples of the other component include a monomer other than di(meth)acrylic monomer (A) and acrylic monomer (B).

In a case in which the photocurable composition contains a monomer other than di(meth)acrylic monomer (A) and acrylic monomer (B) as the other component, the content of the monomer as the other component is preferably 50% by mass or less, more preferably 30% by mass or less, still more preferably 20% by mass or less, and particularly preferably 10% by mass or less, with respect to the total mass of di(meth)acrylic monomer (A) and acrylic monomer (B).

Examples of the other component include a colorant, a coupling agent such as a silane coupling agent (for example, 3-acryloxypropyltrimethoxysilane), additives such as a rubber agent, an ion trapping agent, an ion exchange agent, a leveling agent, a plasticizer, and a defoaming agent, a thermal polymerization initiator, and the like.

In a case in which the photocurable composition of the disclosure contains the thermal polymerization initiator, it is possible to combine photocuring and thermal curing for use. Examples of the thermal polymerization initiator include a thermal radical generator, an amine compound, and the like.

Examples of the other component include an inorganic filler.

However, from the viewpoint of further improving the shape accuracy of the cured product, the photocurable composition of the disclosure preferably contains no inorganic filler (for example, silica, barium borosilicate glass, and the like. The same applies hereinafter.), or in the case of containing an inorganic filler, the content of the inorganic filler with respect to the total amount of the photocurable composition is preferably 60% by mass or less (more preferably 40% by mass or less, still more preferably 20% by mass or less, and even still more preferably 10% by mass or less).

The method of preparation of the photocurable composition of the disclosure is not particularly limited.

Examples of the method for preparing a photocurable composition of the disclosure include a method for mixing di(meth)acrylic monomer (A), acrylic monomer (B), and the photopolymerization initiator (and other components if necessary).

The means of mixing each component is not particularly limited, and examples thereof include a means such as dissolution by ultrasonic waves, a twin-arm stirrer, a roll mixer, a twin-screw extruder, a ball mill mixer, or a planetary stirrer.

The photocurable composition of the present embodiment may be prepared by mixing each component, then removing impurities from the mixture with a filter, and further applying vacuum degassing treatment thereto.

<Preferred Viscosity of Photocurable Composition>

The photocurable composition of the disclosure preferably has a viscosity of from 5 mPa·s to 6,000 mPa·s as measured by an E-type viscometer under the conditions of 25° C. and 50 rpm (hereinafter also simply referred to as "viscosity").

Here, rpm refers to revolutions per minute.

In a case of the viscosity being from 5 mPa·s to 6,000 mPa·s, the photocurable composition is excellent in handleability thereof upon production of the cured product (in particular the photofabrication product).

The viscosity is more preferably from 10 mPa·s to 5,000 mPa·s, still more preferably from 20 mPa·s to 5,000 mPa·s, and even still more preferably from 100 mPa·s to 4,500 mPa·s.

[Cured Product]

The cured product of the disclosure is the cured product of the photocurable composition of the disclosure described above.

Therefore, the cured product of the disclosure is excellent in crack resistance.

The cured product of the disclosure is preferably a cured product by photofabrication (i.e., the photofabrication product).

The method for producing the cured product (i.e., the photofabrication product) is as described above.

[Dental Products]

The dental products of the disclosure include the cured product of the disclosure described above.

Therefore, the dental products of the disclosure are excellent in crack resistance.

Specific examples of the dental products are as described above.

As described above, the dental products are preferably medical device used in an oral cavity and particularly preferably partial dentures.

EXAMPLES

Examples of the disclosure will be described below; however, the disclosure is not limited to the following Examples.

Examples 1 to 39, Comparative Examples 1 to 11

<Preparation of Photocurable Compositions>
Each component shown in Tables 1 to 5 was mixed to obtain each photocurable composition.
<Measurement and Evaluation>
Using the photocurable compositions obtained, the following measurement and evaluation were conducted.
The results are shown in Tables 1 to 5.

(Viscosity of Photocurable Composition)
The viscosity of each of the photocurable compositions obtained was measured with an E-type viscometer at 25° C. and 50 rpm.

(Total Fracture Work of Test Piece P1)
Using each photocurable composition obtained, a test piece P1 was produced by the method described above, and the total fracture work of test piece P1 obtained was measured by the method described above.

(Flexural Modulus of Test Piece P2)
Using each photocurable composition obtained, a test piece P2 was produced by the method described above, and the flexural modulus of test piece P2 obtained was measured by the method described above.

(Flexural Strength of Test Piece P2)
Using each photocurable composition obtained, test piece P2 was produced by the method described above, and the flexural strength of test piece P2 obtained was measured by the method described above.

| | | | Number of functional groups | Mw | Example 1 | Example 2 | Example 3 | Example 4 | Example 5 | Example 6 | Example 7 | Example 8 | Example 9 | Example 10 |
|---|---|---|---|---|---|---|---|---|---|---|---|---|---|---|
| Composition | Di(meth)acrylic monomer (A) | UDA | 2 | 443 | | | | | | 550 | 700 | 800 | | |
| | | UDMA | 2 | 471 | | | | | 550 | | | | | |
| | | AH-600 | 2 | 613 | 500 | 550 | 600 | 600 | | | | | | |
| | | MMD-352 | 2 | 633 | | | | | | | | | | |
| | | KRM-060 | 2 | 448 | | | | | | | | | 500 | 550 |
| | | KRM-077 | 2 | 438 | | | | | | | | | | |
| | | U-2PPA | 2 | 500 | | | | | | | | | | |
| | | UA-160TM | 2 | 1600 | | | | | | | | | | |
| | | UN-352 | 2 | 3000 | | | | | | | | | | |
| | Acrylic monomer (B) | IB-XA | 1 | 208 | | | | | | | | | | |
| | | POB-A | 1 | 254 | 400 | 250 | 350 | 400 | | 450 | | | | |
| | | A-LEN-10 | 1 | 268 | | 200 | | | | | | | | |
| | | ACMO | 1 | 141 | | | 50 | | | | | | | |
| | | PO-A | 1 | 192 | | | | | | | | | 500 | |
| | | V216 | 1 | 215 | | | | | | | 300 | | | |
| | | 4-HBA | 1 | 144 | | | | | | | | | | |
| | | MEDOL10 | 1 | 200 | | | | | | | | | | |
| | | 2-HPA | 1 | 130 | | | | | | | | 200 | | |
| | | P2H-A | 1 | 236 | | | | | 450 | | | | | 450 |
| | | FA513AS | 1 | 206 | | | | | | | | | | |
| | Other (meth)acrylic monomer | IB-X | 1 | 222 | 100 | | | | | | | | | |
| | Photopolymerization initiator | Omnirad 819 | | | 10 | 10 | 10 | 10 | 10 | 10 | 10 | 10 | 10 | 10 |
| | | Omnirad 184 | | | | | | | | | | | | |
| | | Omnirad TPO | | | | | | | | | | | | |
| Proportion of number of acryloyl groups (%) | | | | | 89 | 100 | 100 | 100 | 45 | 100 | 100 | 100 | 100 | 100 |
| Viscosity (mPa·s) | | | | | 363 | 1034 | 1009 | 1017 | 150 | 225 | 731 | 575 | 205 | 422 |
| Flexural strength of test piece P2 (MPa) | | | | | 9 | 8 | 17 | 9 | 6 | 28 | 22 | 42 | 55 | 7 |
| Flexural modulus of test piece P2 (MPa) | | | | | 511 | 733 | 1124 | 257 | 69 | 1345 | 653 | 1168 | 2244 | 82 |
| Total fracture work of test piece P1 (J/m$^2$) | | | | | 3137 | 2755 | 2124 | 2638 | 1404 | 1746 | 1548 | 1872 | 1466 | 2972 |

TABLE 2

| Composition | | | Number of functional groups | Mw | Example 11 | Example 12 | Example 13 | Example 14 | Example 15 | Example 16 | Example 17 | Example 18 | Example 19 | Example 20 |
|---|---|---|---|---|---|---|---|---|---|---|---|---|---|---|
| Composition | Di(meth)acrylic monomer (A) | UDA | 2 | 443 | | | | | | | | | | |
| | | UDMA | 2 | 471 | | | | | | | | | | |
| | | AH-600 | 2 | 613 | | | | | | | | | | |
| | | MMD-352 | 2 | 633 | | | | 540 | 480 | | 300 | 330 | 350 | 350 |
| | | KRM-060 | 2 | 448 | | | | | | | | | | |
| | | KRM-077 | 2 | 438 | 450 | | | | | | | | | |
| | | U-2PPA | 2 | 500 | | 500 | 500 | | | | | | | |
| | | UA-160TM | 2 | 1600 | | | | 100 | 200 | 400 | | | | |
| | | UN-352 | 2 | 3000 | | | | | | | | | | |
| | Acrylic monomer (B) | IB-XA | 1 | 208 | | | | | | 600 | | | | |
| | | POB-A | 1 | 254 | | | | 360 | 320 | | 200 | 270 | 250 | 350 |
| | | A-LEN-10 | 1 | 268 | | | | | | | 500 | 400 | 400 | 300 |
| | | ACMO | 1 | 141 | | | | | | | | | | |
| | | PO-A | 1 | 192 | 550 | | | | | | | | | |
| | | V216 | 1 | 215 | | | 500 | | | | | | | |
| | | 4-HBA | 1 | 144 | | | | | | | | | | |
| | | MEDOL10 | 1 | 200 | | | | | | | | | | |
| | | 2-HPA | 1 | 130 | | | | | | | | | | |
| | | P2H-A | 1 | 236 | | 500 | | | | | | | | |
| | | FA513AS | 1 | 206 | | | | | | | | | | |
| | Other (meth)acrylic monomer | IB-X | 1 | 222 | | | | | | | | | | |
| | Photo-polymerization initiator | Omnirad 819 | | | 10 | 10 | 10 | 10 | 10 | 10 | 10 | 10 | 10 | 10 |
| | | Omnirad 184 | | | | | | | | | | | | |
| | | Omnirad TPO | | | | | | | | | | | | |
| Proportion of number of acryloyl groups (%) | | | | | 100 | 100 | 100 | 100 | 100 | 100 | 100 | 100 | 100 | 100 |
| Viscosity (mPa·s) | | | | | 105 | 173 | 361 | 3260 | 4920 | 435 | 430 | 446 | 535 | 395 |
| Flexural strength of test piece P2 (MPa) | | | | | 35 | 7 | 9 | 10 | 4 | 7 | 5 | 6 | 9 | 3 |
| Flexural modulus of test piece P2 (MPa) | | | | | 1594 | 84 | 141 | 310 | 34 | 200 | 287 | 547 | 1221 | 71 |
| Total fracture work of test piece P1 (J/m$^2$) | | | | | 1860 | 1958 | 2193 | 2857 | 3559 | 6086 | 2338 | 4507 | 4582 | 5430 |

TABLE 3

| Composition | | | Number of functional groups | Mw | Example 21 | Example 22 | Example 23 | Example 24 | Example 25 | Example 26 | Example 27 | Example 28 | Example 29 | Example 30 |
|---|---|---|---|---|---|---|---|---|---|---|---|---|---|---|
| Composition | Di(meth)acrylic monomer (A) | UDA | 2 | 443 | | | | | | | | | | |
| | | UDMA | 2 | 471 | | | | | | | | | | |
| | | AH-600 | 2 | 613 | | | | | | | | | | |
| | | MMD-352 | 2 | 633 | 400 | 400 | 470 | 500 | 500 | 530 | 540 | 600 | 620 | 600 |
| | | KRM-060 | 2 | 448 | | | | | | | | | | |
| | | KRM-077 | 2 | 438 | | | | | | | | | | |
| | | U-2PPA | 2 | 500 | | | | | | | | | | |
| | | UA-160TM | 2 | 1600 | | | | | | | | | | |
| | | UN-352 | 2 | 3000 | | | | | | | | | | |
| | Acrylic monomer (B) | IB-XA | 1 | 208 | | | | | | | | | | |
| | | POB-A | 1 | 254 | 400 | 500 | 530 | 450 | 500 | 470 | 135 | 150 | 200 | 400 |
| | | A-LEN-10 | 1 | 268 | 200 | | | | | | | | | |
| | | ACMO | 1 | 141 | | 100 | | | | | | | | |
| | | PO-A | 1 | 192 | | | | | | | | | | |
| | | V216 | 1 | 215 | | | | | | | | | | |
| | | 4-HBA | 1 | 144 | | | | | | | | | | |
| | | MEDOL10 | 1 | 200 | | | | | | | 325 | | | |
| | | 2-HPA | 1 | 130 | | | | | | | | | | |
| | | P2H-A | 1 | 236 | | | | | | | | 250 | 180 | |
| | | FA513AS | 1 | 206 | | | | 50 | | | | | | |
| | Other (meth)acrylic monomer | IB-X | 1 | 222 | | | | | | | | | | |
| | Photo-polymerization initiator | Omnirad 819 | | | 10 | 10 | 10 | 10 | 10 | 10 | 10 | 10 | 10 | 10 |
| | | Omnirad 184 | | | | | | | | | | | | |
| | | Omnirad TPO | | | | | | | | | | | | |

TABLE 3-continued

|  | Number of functional groups | Mw | Example 21 | Example 22 | Example 23 | Example 24 | Example 25 | Example 26 | Example 27 | Example 28 | Example 29 | Example 30 |
|---|---|---|---|---|---|---|---|---|---|---|---|---|
| Proportion of number of acryloyl groups (%) |  |  | 100 | 100 | 100 | 100 | 100 | 100 | 100 | 100 | 100 | 100 |
| Viscosity (mPa·s) |  |  | 471 | 241 | 437 | 570 | 592 | 890 | 418 | 1220 | 1640 | 937 |
| Flexural strength of test piece P2 (MPa) |  |  | 4 | 20 | 5 | 34 | 10 | 18 | 5 | 5 | 6 | 32 |
| Flexural modulus of test piece P2 (MPa) |  |  | 107 | 1279 | 516 | 2081 | 591 | 1758 | 129 | 304 | 98 | 1923 |
| Total fracture work of test piece P1 (J/m$^2$) |  |  | 4454 | 3158 | 3312 | 1355 | 3041 | 2271 | 4681 | 2981 | 2308 | 1217 |

TABLE 4

| | | | Number of functional groups | Mw | Example 31 | Example 32 | Example 33 | Example 34 | Example 35 | Example 36 | Example 37 | Example 38 | Example 39 |
|---|---|---|---|---|---|---|---|---|---|---|---|---|---|
| Composition | Di(meth)acrylic monomer (A) | UDA | 2 | 443 | | | | | | | | | |
| | | UDMA | 2 | 471 | | | | | | | | | |
| | | AH-600 | 2 | 613 | | | | | | | 500 | | |
| | | MMD-352 | 2 | 633 | 656 | 680 | | | | | | 540 | |
| | | KRM-060 | 2 | 448 | | | | | | | | | |
| | | KRM-077 | 2 | 438 | | | | | | | | | 450 |
| | | U-2PPA | 2 | 500 | | | | | | | | | |
| | | UA-160TM | 2 | 1600 | | | | | | | | 100 | |
| | | UN-352 | 2 | 3000 | | | 400 | 400 | 400 | 400 | | | |
| | Acrylic monomer (B) | IB-XA | 1 | 208 | | | 300 | 400 | 300 | 400 | | | |
| | | POB-A | 1 | 254 | 164 | 170 | | | | | 400 | 360 | |
| | | A-LEN-10 | 1 | 268 | | | 200 | 200 | 200 | 200 | | | |
| | | ACMO | 1 | 141 | | | 100 | | 100 | | | | |
| | | PO-A | 1 | 192 | | | | | | | | | 550 |
| | | V216 | 1 | 215 | | | | | | | | | |
| | | 4-HBA | 1 | 144 | 180 | 150 | | | | | | | |
| | | MEDOL10 | 1 | 200 | | | | | | | | | |
| | | 2-HPA | 1 | 130 | | | | | | | | | |
| | | P2H-A | 1 | 236 | | | | | | | | | |
| | | FA513AS | 1 | 206 | | | | | | | | | |
| | Other (meth)acrylic monomer | IB-X | 1 | 222 | | | | | | | | 100 | |
| | Photo-polymerization initiator | Omnirad 819 | | | 10 | 10 | 10 | 10 | 10 | 10 | | | |
| | | Omnirad 184 | | | | | | | | | 10 | 10 | 10 |
| | | Omnirad TPO | | | | | | | | | 10 | 10 | 10 |
| Proportion of number of acryloyl groups (%) | | | | | 100 | 100 | 100 | 100 | 100 | 100 | 89 | 100 | 100 |
| Viscosity (mPa·s) | | | | | 1022 | 1590 | 466 | 493 | 702 | 667 | 355 | 3130 | 110 |
| Flexural strength of test piece P2 (MPa) | | | | | 17 | 25 | 9 | 6 | 8 | 4 | 10 | 11 | 37 |
| Flexural modulus of test piece P2 (MPa) | | | | | 877 | 1094 | 103 | 282 | 94 | 39 | 522 | 324 | 1623 |
| Total fracture work of test piece P1 (J/m$^2$) | | | | | 3043 | 1592 | 10472 | 8500 | 6435 | 7032 | 3016 | 2755 | 1774 |

TABLE 5

| | | Number of functional groups | Mw | Comparative Example 1 | Comparative Example 2 | Comparative Example 3 | Comparative Example 4 | Comparative Example 5 | Comparative Example 6 | Comparative Example 7 | Comparative Example 8 | Comparative Example 9 | Comparative Example 10 | Comparative Example 11 |
|---|---|---|---|---|---|---|---|---|---|---|---|---|---|---|
| Di(meth)acrylic monomer (A) | UDA | 2 | 443 | | | | | | | | | | | 700 |
| | UDMA | 2 | 471 | 700 | | | | | | | | | 550 | |
| Multifunctional (meth)acrylate | E4100 | 3 | 1100 | | 700 | | | | | | | | | |
| | E4740 | 3 | 1250 | | | 700 | | | | | | | | |
| | UA-306T | 6 | 771 | | | | 600 | 630 | 630 | | | | | |
| | UA-306H | 6 | 765 | | | | | | | 650 | 650 | 450 | | |

TABLE 5-continued

|  |  | Number of functional groups | Mw | Comparative Example 1 | Comparative Example 2 | Comparative Example 3 | Comparative Example 4 | Comparative Example 5 | Comparative Example 6 | Comparative Example 7 | Comparative Example 8 | Comparative Example 9 | Comparative Example 10 | Comparative Example 11 |
|---|---|---|---|---|---|---|---|---|---|---|---|---|---|---|
| Acrylic monomer (B) | POB-A | 1 | 254 |  | 300 | 300 |  |  | 200 |  | 200 | 550 |  |  |
|  | PO-A | 1 | 192 |  |  |  | 400 |  |  |  |  |  |  | 300 |
| Other (meth)acrylic monomer | 4EG-A | 2 | 302 |  |  |  |  | 370 | 170 | 350 | 150 |  |  |  |
| Photo-polymerization initiator | HEMA | 1 | 130 | 300 |  |  |  |  |  |  |  |  |  |  |
|  | PO | 1 | 206 |  |  |  |  |  |  |  |  |  | 450 |  |
|  | Omnirad 819 |  |  | 10 | 10 | 10 | 10 | 10 | 10 | 10 | 10 | 10 | 10 | 10 |
| Proportion of number of acryloyl groups (%) |  |  |  | 0 | 100 | 100 | 100 | 100 | 100 | 100 | 100 | 100 | 0 | 100 |
| Viscosity (mPa · s) |  |  |  | 192 | 1140 | 1200 | 260 | 407 | 560 | 409 | 548 | 310 | 112 | 309 |
| Flexural strength of test piece P2 (MPa) |  |  |  | 87 | 3 | 3 | 85 | 80 | 77 | 53 | 71 | 94 | 80 | 51 |
| Flexural modulus of test piece P2 (MPa) |  |  |  | 2460 | 37 | 30 | 3687 | 3811 | 3253 | 2801 | 3430 | 2998 | 2361 | 1530 |
| Total fracture work of test piece P1 (J/m²) |  |  |  | 123 | 22 | 160 | 13 | 22 | 17 | 25 | 16 | 16 | 40 | 958 |

In Tables 1 to 5, the number in the "Composition" column in each Example and each Comparative Example refers to parts by mass, and the blank column refers to containing no corresponding component.

In Tables 1 to 5, the number in the "Proportion of number of acryloyl groups (%)" column in each Example and each Comparative Example indicates the proportion (%) of the number of acryloyl groups with respect to the total number of acryloyl groups and methacryloyl groups in the photocurable composition.

<Di(Meth)Acrylic Monomer (A)>

In Tables 1 to 5, di(meth)acrylic monomer (A) (i.e., a compound having two (meth)acryloyloxy groups and two urethane bonds; i.e., a bifunctional urethane (meth)acrylate) is, specifically the following compounds.

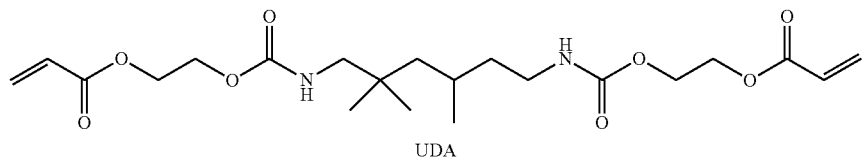

UDA

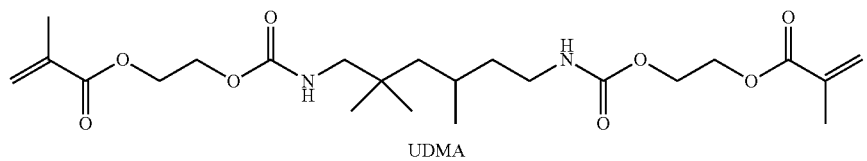

UDMA

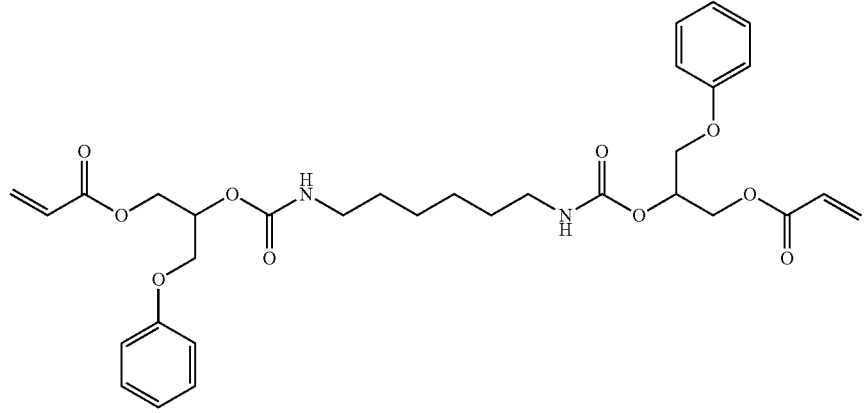

AH-600

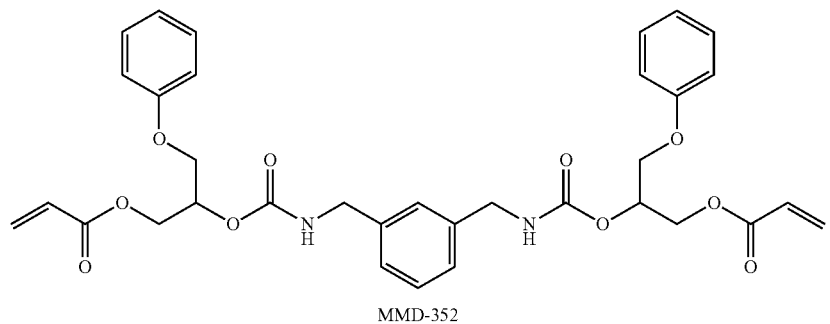 [SMILES: C=CC(=O)OCC(COc1ccccc1)OC(=O)NCc1cccc(CNC(=O)OC(COC(=O)C=C)COc2ccccc2)c1]

MMD-352

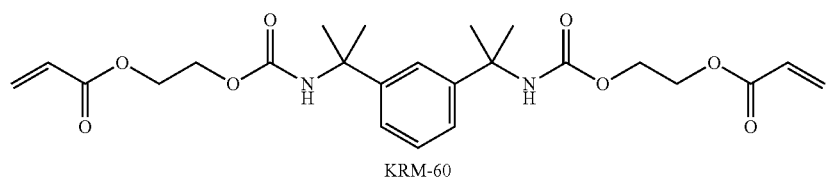

KRM-60

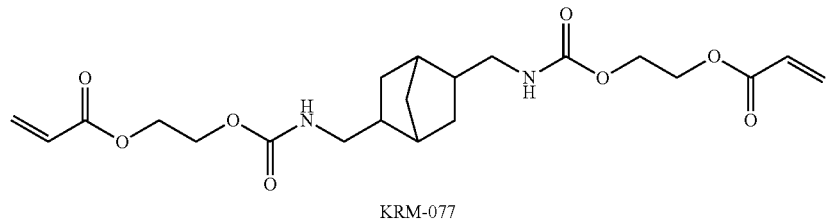

KRM-077

UDA: The compound produced according to Production Example 1 below.
UDMA: The compound produced according to Production Example 2 below.
AH-600: A compound manufactured by KYOEISHA CHEMICAL Co., LTD.
MMD-352: The compound produced according to Production Example 3 below.
KRM-060: The compound produced according to Production Example 4.
KRM-077: The compound produced according to Production Example 5.
U-2PPA: A bifunctional urethane acrylate manufactured by SHIN NAKAMURA CHEMICAL CO., LTD.
UA-160™: A bifunctional urethane acrylate manufactured by SHIN NAKAMURA CHEMICAL CO., LTD.
UN-352: A bifunctional urethane acrylate manufactured by Negami Chemical Industrial Co., Ltd.
Production Examples 1 to 5 will be described below.
Incidentally, the abbreviations in each Production Example are as follows.
HEA: Hydroxyethyl acrylate
TMHDI: 2,4,4-Trimethylhexane diisocyanate
DBTDL: Dibutyl tin dilaurate
MEHQ: 4-Methoxyphenol
HEMA: Hydroxyethyl methacrylate
M-600A: 2-Hydroxy-3-phenoxypropyl acrylate
TMXDI: 1,3-Tetramethylxylylene diisocyanate
XDI: m-Xylylene diisocyanate
NBDI: Norbornene diisocyanate Production Example 1: Production of UDA In a four-necked flask of 1 liter equipped with a well-dried stirring blade and a thermometer, 372 g (3.20 mol) of HEA, 0.71 g of DBTDL (0.1% by mass with respect to the total mass of HEA and TMHDI), and 0.35 g of MEHQ (0.05% by mass of the total mass of HEA and TMHDI) were added and stirred until the mixture was homogeneous, and then the temperature was raised to 60° C. Subsequently, 337 g of TMHDI (1.60 mol) was added dropwise over 1 hour. As the internal temperature rose due to the reaction heat during the drop, the drop rate was controlled so that the temperature was below 80° C. After completion of the dropping of the total amount, the reaction was carried out for 10 hours while keeping the temperature at 80° C. At this time, the proceedings of reaction were tracked by HPLC analysis to confirm the endpoint of the reaction. The product was discharged from the reactor to obtain 680 g of a bifunctional urethane acrylate (UDA). The viscosity at 25° C. was 7,100 mPa·s.

Production Example 2: Production of UDMA

In a four-necked flask of 1 liter equipped with a well-dried stirring blade and a thermometer, 416 g (3.20 mol) of HEMA, 0.75 g of DBTDL (0.1% by mass with respect to the total mass of HEMA and TMHDI), and 0.38 g of MEHQ (0.05% by mass of the total mass of HEMA and TMHDI) were added and stirred until the mixture was homogeneous, and then the temperature was raised to 60° C. Subsequently, 337 g of TMHDI (1.60 mol) was added dropwise over 1 hour. As the internal temperature rose due to the reaction heat during the drop, the drop rate was controlled so that the temperature was below 80° C. After completion of the dropping of the total amount, the reaction was carried out for 10 hours while keeping the temperature at 80° C. At this time, the proceedings of reaction were tracked by HPLC analysis to confirm the endpoint of the reaction. The product was discharged from the reactor to obtain 720 g of a bifunctional urethane methacrylate (UDMA). The viscosity at 25° C. was 8,200 mPa·s.

Production Example 3: Production of MMD-352

In a four-necked flask of 1 liter equipped with a well-dried stirring blade and a thermometer, 444 g (2.00 mol) of M-600A, 0.63 g of DBTDL (0.10% by mass with respect to the total mass of M-600A and XDI), and 0.32 g of MEHQ (0.05% by mass of the total mass of M-600A and XDI) were added and stirred until the mixture was homogeneous, and then the temperature was raised to 60° C. Subsequently, 188 g of XDI (1.00 mol) was added dropwise over 1 hour. As the internal temperature rose due to the reaction heat during the drop, the drop rate was controlled so that the temperature was below 80° C. After completion of the dropping of the total amount, the reaction was carried out for 10 hours while keeping the temperature at 80° C. At this time, the proceedings of reaction were tracked by HPLC analysis to confirm the endpoint of the reaction. The product was discharged from the reactor to obtain 600 g of a bifunctional urethane acrylate (MMD-352). The viscosity at 65° C. was 6,210 mPa·s.

Production Example 4: Production of KRM-060

In a four-necked flask of 1 liter equipped a well-dried stirring blade and a thermometer, 232 g (2.00 mol) of HEA, 0.48 g of DBTDL (0.1% by mass with respect to the total mass of HEA and TMXDI), and 0.24 g of MEHQ (0.05% by mass of the total mass of HEA and TMXDI) were added and stirred until the mixture was homogeneous, and then the temperature was raised to 60° C. Subsequently, 244 g of TMXDI (1.00 mol) was added dropwise over 1 hour. As the internal temperature rose due to the reaction heat during the drop, the drop rate was controlled so that the temperature was below 80° C. After completion of the dropping of the total amount, the reaction was carried out for 10 hours while keeping the temperature at 80° C. At this time, the proceedings of reaction were tracked by HPLC analysis to confirm the endpoint of the reaction. The product was discharged from the reactor to obtain 455 g of a bifunctional urethane acrylate (KRM-060). The viscosity at 65° C. was 2,200 mPa·s.

Production Example 5: Production of KRM-077

In a four-necked flask of 1 liter equipped a well-dried stirring blade and a thermometer, 372 g (3.20 mol) of HEA, 0.70 g of DBTDL (0.1% by mass with respect to the total mass of HEA and NBDI), and 0.35 g of MEHQ (0.05% by mass of the total mass of HEA and NBDI) were added and stirred until the mixture was homogeneous, and then the temperature was raised to 60° C. Subsequently, 330 g of NBDI (1.60 mol) was added dropwise over 1 hour. As the internal temperature rose due to the reaction heat during the drop, the drop rate was controlled so that the temperature was below 80° C. After completion of the dropping of the total amount, the reaction was carried out for 10 hours while keeping the temperature at 80° C. At this time, the proceedings of reaction were tracked by HPLC analysis to confirm the endpoint of the reaction. The product was discharged from the reactor to obtain 670 g of a bifunctional urethane acrylate (KRM-077). The viscosity at 65° C. was 930 mPa·s.

<Multifunctional (Meth)Acrylate>

In Tables 1 to 5, the multifunctional (meth)acrylates are the following compounds.

E4100: A trifunctional urethane acrylate "EBECRYL4100" manufactured by DAICEL-ALLNEX LTD.

E4740: A trifunctional urethane acrylate "EBECRYL4740" manufactured by DAICEL-ALLNEX LTD.

UA-306T: A hexafunctional urethane acrylate manufactured by KYOEISHA CHEMICAL Co., LTD.

UA-306H: A hexafunctional urethane acrylate manufactured by KYOEISHA CHEMICAL Co., LTD.

<Acrylic Monomer (B)

In Tables 1 to 5, acrylic monomers (B) (i.e., the compounds having one acryloyl group; i.e., the monofunctional acrylic monomers) are, specifically the following compounds.

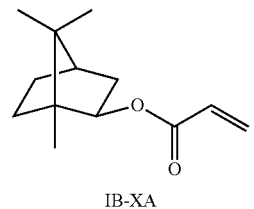

IB-XA

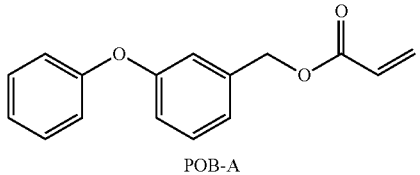 [SMILES: C=CC(=O)OCc1cccc(Oc2ccccc2)c1]

POB-A

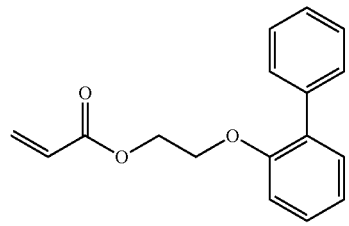

A-LEN-10

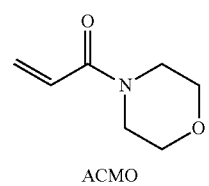

ACMO

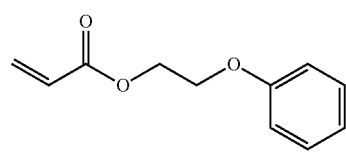

PO-A

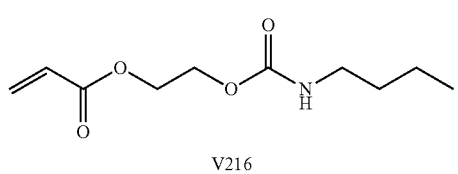

V216

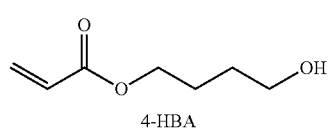

4-HBA

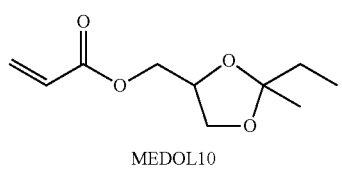

MEDOL10

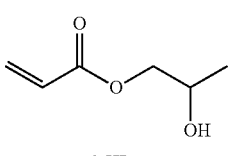

2-HPA

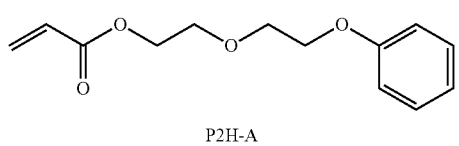 [SMILES: C=CC(=O)OCCOCCOc1ccccc1]

P2H-A

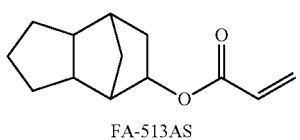

FA-513AS

IB-XA: A compound manufactured by KYOEISHA CHEMICAL Co., LTD.

POB-A: A compound manufactured by KYOEISHA CHEMICAL Co., LTD.

A-LEN-10: A compound manufactured by SHIN NAKAMURA CHEMICAL CO., LTD.

ACMO: A compound manufactured by KJ Chemicals Corporation.

PO-A: A compound manufactured by KYOEISHA CHEMICAL Co., LTD.

V216: A compound manufactured by OSAKA ORGANIC CHEMICAL INDUSTRY LTD. 4-HBA: A compound manufactured OSAKA ORGANIC CHEMICAL INDUSTRY LTD.

MEDOL10: A compound manufactured by OSAKA ORGANIC CHEMICAL INDUSTRY LTD.

2-HPA: A compound manufactured by KYOEISHA CHEMICAL Co., LTD.

P2H-A: A compound manufactured by KYOEISHA CHEMICAL Co., LTD.

FA513AS: A compound manufactured by Hitachi Chemical Company, Ltd.

<Other (Meth)Acrylic Monomers>

In Tables 1 to 5, "Other (meth)acrylic monomer" refers to bifunctional (meth)acrylic monomers other than di(meth)acrylic monomer (A) and acrylic monomer (B) and are, specifically the following compounds.

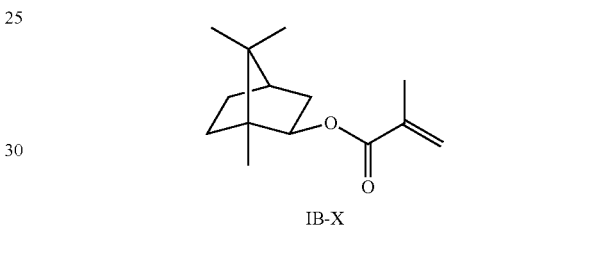

IB-X

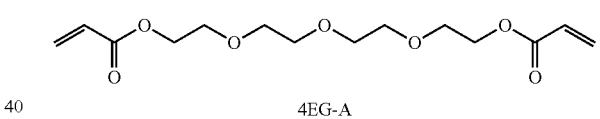

4EG-A

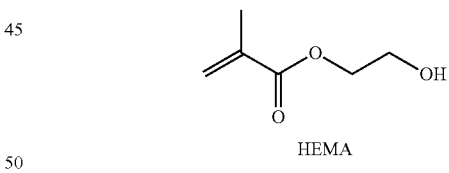

HEMA

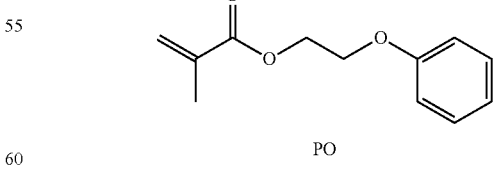

PO

IB-X: A compound manufactured by KYOEISHA CHEMICAL Co., LTD.

4EG-A: A compound manufactured by KYOEISHA CHEMICAL Co., LTD.

HEMA: A compound manufactured by KYOEISHA CHEMICAL Co., LTD.

PO: A compound manufactured by KYOEISHA CHEMICAL Co., LTD.

<Photopolymerization Initiators>

The photopolymerization initiators in Tables 1 to 5 are as follows.

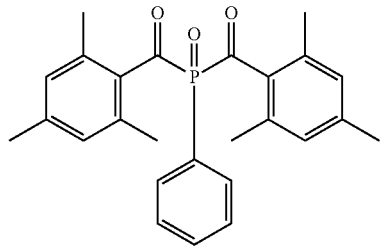

Omnirad 819

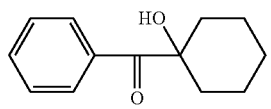

Omnirad 184

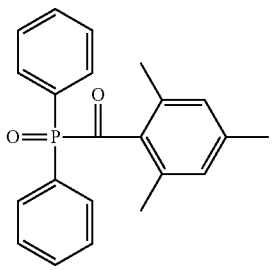

Omnirad TPO

Omnirad 819: Omnirad 819 manufactured by IGM Resins B.V. (acylphosphine oxide-based compound)

Omnirad 184: Omnirad 184 manufactured by IGM Resins B.V. (alkylphenone-based compound)

Omnirad TPO: Omnirad TPO manufactured by IGM Resins B.V. (acylphosphine oxide-based compound).

As shown in Tables 1 to 5, the photocurable composition in each Example contains the photopolymerizable component and the photopolymerization initiator, and the total fracture work of test piece P1 was 1100 J/m$^2$ or more. Therefore, the photocurable composition of each Example is expected to enable production of a cured product excellent in crack resistance (i.e., resistance to cracking).

In contrast, the photocurable composition of each Comparative Example had a total fracture work of test piece P1 of less than 1100 J/m$^2$.

<Indentation Test>

The following indentation test was conducted in order to confirm whether cracks or fissures occur upon fitting of the partial denture produced by the photocurable composition of the disclosure.

The following indentation test is a test in which an indentation load perpendicular to the longitudinal direction and parallel to the thickness direction of the rectangular test piece is applied to the center portion in the longitudinal direction thereof, i.e., the test simulates a load applied upon fitting of a partial denture.

(Producing of Test Piece P3)

In the indentation test, a test piece P3 produced by the photocurable composition of each of Examples 1 to 39 and Comparative Examples 1 to 11, was used.

Test piece P3 was a rectangular test piece with a length of 64 mm, a width of 10 mm, and a thickness of 4 mm, and was produced by the following method.

Test piece P3 was produced as follows: Each of the photocurable compositions of Examples 1 to 39 and Comparative Examples 1 to 11, was irradiated with visible light of wavelength of 405 nm at an irradiation dose of 12 mJ/cm$^2$ to form a cured layer P1 with a thickness of 100 µm, and the cured layer P1 was stacked in the thickness direction thereof to form a rectangular fabrication product P3 with a length of 64 mm, a width of 10 mm, and a thickness of 4 mm. Then fabrication product P3 underwent photofabrication under the irradiation conditions of ultraviolet rays of wavelength of 365 nm at an irradiation dose of 10 J/cm$^2$ to obtain test piece P3 above.

The photofabrication apparatus used for producing of test piece P3 in this indentation test was the DLP type 3D printer, "Cara Print4.0" manufactured by Kulzer GmbH.

(Indentation Test)

The indentation test of test piece P3 was carried out in compliance with ISO 20795-1: 2008 for measurement of flexural strength and flexural modulus. Specifically, the universal testing machine (manufactured by INTESCO Co., Ltd.) was used and the test was carried out as follows.

Two support pins with a hemispherical tip of 3.2 mm in diameter were prepared as fulcrums to support a test piece. These two support pins were arranged in parallel so that the distance between fulcrums (i.e., the distance between tips) was 50±0.1 mm.

Next, test piece P3 was mounted on the two support pins so that test piece P3 was supported by the fulcrum (i.e., the tip) of each support pin. In this case, the test piece was arranged so that the center between the two fulcrums coincided with the center portion in the longitudinal direction of the rectangular test piece P3.

Next, a load plunger with a hemispherical tip of 3.2 mm in diameter was prepared.

Subsequently, a load perpendicular to the longitudinal direction of test piece P3 and parallel to the thickness direction of test piece P3, was applied by the tip of the load plunger to the center portion in the longitudinal direction of test piece P3 mounted on the two test pins. The speed at which the indentation load was applied was 5±1 mm/min. The atmospheric temperature upon application of the indentation load was 23° C.

When the indentation amount (i.e., the distance traveled by the tip of the load plunger) reached 10 mm, the application of the indentation load was completed, and then test piece P3 was visually observed to check presence or absence of cracks.

(Results)

In each of Examples 1 to 39, where the total fracture work of test piece P1 was 1100 J/m$^2$ or more, no cracks occurred in test piece P3 in the indentation test above.

In each of Comparative Examples 1 to 11, where the total fracture work of test piece P1 was less than 1100 J/m$^2$, cracks occurred in test piece P3 in the aforementioned indentation test.

From above all, in a case in which the cured product of the photocurable composition of the present disclosure having a total fracture work of 1100 J/m² or more as is the case of test piece P1, was used as a dental product such as a partial denture, cracks of the cured products upon the fitting were found to be inhibited.

The disclosure of Japanese Patent Application No. 2020-058696, filed Mar. 27, 2021, is incorporated herein by reference in their entirety.

All references, patent applications, and technical standards cited in the present description are herein incorporated by reference to the same extent that each individual reference, patent application, and technical standard were specifically and individually indicated to be incorporated by reference.

The invention claimed is:

1. A photocurable composition comprising a photopolymerizable component and a photopolymerization initiator, wherein:
in a case in which a test piece P1 with a length of 39 mm, a width of 8 mm, and a thickness of 4 mm, is produced by photofabrication under conditions in which the photocurable composition is irradiated with visible light having a wavelength of 405 nm at an irradiation dose of 12 mJ/cm² to form a cured layer P1 with a thickness of 100 m, the cured layer P1 is stacked in a thickness direction thereof to form a rectangular fabrication product P1 with a length of 39 mm, a width of 8 mm, and a thickness of 4 mm, and the fabrication product P1 is irradiated with ultraviolet rays having a wavelength of 365 nm at an irradiation dose of 10 J/cm² to produce the test piece P1, a total fracture work of the test piece P1 measured in compliance with ISO20795-1:2008 is 1100 J/m² or more;
wherein the photopolymerizable component comprises:
a di(meth)acrylic monomer (A) having two (meth)acryloyloxy groups and two urethane bonds; and
an acrylic monomer (B) having one acryloyl group; and
wherein di(meth)acrylic monomer (A) comprises a compound represented by the following Formula (1),

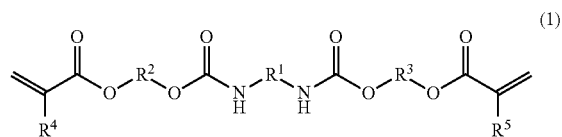

wherein, in Formula (1), $R^1$ is a divalent chain hydrocarbon group, a divalent hydrocarbon group with an aromatic structure, or a divalent hydrocarbon group with an alicyclic structure: each of $R^2$ and $R^3$ is independently a divalent chain hydrocarbon group that may have a substituent; and each of $R^4$ and $R^5$ is independently a methyl group or a hydrogen atom.

2. The photocurable composition according to claim 1, wherein:
in a case in which a test piece P2 with a length of 64 mm, a width of 10 mm, and a thickness of 3.3 mm, is produced by photofabrication under conditions in which the photocurable composition is irradiated with visible light having a wavelength of 405 nm at an irradiation dose of 12 mJ/cm² to form a cured layer P2 with a thickness of 100 m, the cured layer P2 is stacked in a thickness direction thereof to form a rectangular fabrication product P2 with a length of 64 mm, a width of 10 mm, and a thickness of 3.3 mm, and the fabrication product P2 is irradiated with ultraviolet rays having a wavelength of 365 nm at an irradiation dose of 10 J/cm² to produce the test piece P2, a flexural modulus of the test piece P2 measured in compliance with ISO20795-1:2008 is 2,500 MPa or less.

3. The photocurable composition according to claim 1, wherein
in a case in which a test piece P2 with a length of 64 mm, a width of 10 mm, and a thickness of 3.3 mm, is produced by photofabrication under conditions in which the photocurable composition is irradiated with visible light having a wavelength of 405 nm at an irradiation dose of 12 mJ/cm² to form a cured layer P2 with a thickness of 100 m, the cured layer P2 is stacked in a thickness direction thereof to form a rectangular fabrication product P2 with a length of 64 mm, a width of 10 mm, and a thickness of 3.3 mm, and the fabrication product P2 is irradiated with ultraviolet rays having a wavelength of 365 nm at an irradiation dose of 10 J/cm² to produce the test piece P2, a flexural strength of the test piece P2 measured in compliance with ISO20795-1:2008 is 70 MPa or less.

4. The photocurable composition according to claim 1, wherein a proportion of a number of acryloyl groups with respect to a total number of acryloyl groups and methacryloyl groups in the photocurable composition is 40% or more.

5. The photocurable composition according to claim 1, wherein, in Formula (1):
$R^1$ is a divalent hydrocarbon group with an aromatic structure, having from 6 to 12 carbon atoms, or a divalent hydrocarbon group with an alicyclic structure, having from 6 to 12 carbon atoms; and
each of $R^2$ and $R^3$ is independently a divalent chain hydrocarbon group having from 2 to 6 carbon atoms and no substituent.

6. The photocurable composition according to claim 1, wherein the acrylic monomer (B) comprises at least one of a compound represented by the following Formula (2) or a compound represented by the following Formula (3),

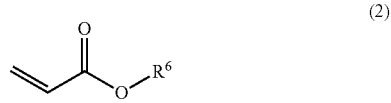

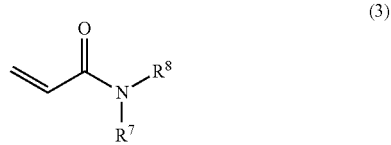

wherein, in Formula (2), $R^6$ is a monovalent organic group that may have a ring structure, and
wherein, in Formula (3), each of $R^7$ and $R^8$ is independently a hydrogen atom or a monovalent organic group that may have a ring structure, and $R^7$ and $R^8$ may form a ring by bonding with each other.

7. The photocurable composition according to claim 6, wherein:
the acrylic monomer (B) comprises the compound represented by Formula (2); and
in Formula (2), $R^6$ is a monovalent organic group with a ring structure, having from 6 to 20 carbon atoms.

8. The photocurable composition according to claim 1, wherein a weight-average molecular weight of the di(meth)acrylic monomer (A) is from 380 to 4,000.

9. The photocurable composition according to claim 1, wherein a weight-average molecular weight of the acrylic monomer (B) is from 130 to 320.

10. The photocurable composition according to claim 1, wherein a content of the di(meth)acrylic monomer (A) is from 200 parts by mass to 850 parts by mass with respect to 1000 parts by mass of a total content of (meth)acrylic monomer components comprised in the photocurable composition.

11. The photocurable composition according to claim 1, wherein a total content of the di(meth)acrylic monomer (A) and the acrylic monomer (B) is 800 parts by mass or more with respect to 1000 parts by mass of a total content of (meth)acrylic monomer components comprised in the photocurable composition.

12. The photocurable composition according to claim 1, having a viscosity of from 20 mPa·s to 5000 mPa·s, measured with an E-type viscometer under conditions of 25° C. and 50 rpm.

13. The photocurable composition according to claim 1, which is a photocurable composition for photofabrication.

14. A cured product of the photocurable composition according to claim 1.

15. A dental product comprising the cured product according to claim 14.

16. The dental product according to claim 15, which is a medical device used in an oral cavity.

17. The photocurable composition according to claim 3, wherein the flexural strength of the test piece P2 measured in compliance with ISO20795-1:2008 is from 3 MPa to 42 MPa.

* * * * *